United States Patent [19]
Smith et al.

[11] Patent Number: 5,408,037
[45] Date of Patent: Apr. 18, 1995

[54] METHODS FOR DETECTING GLUCAGON ANTAGONISTS

[75] Inventors: Robert A. Smith, Seattle; James R. Piggott, Bothell, both of Wash.

[73] Assignee: ZymoGenetics, Inc., Seattle, Wash.

[21] Appl. No.: 741,931

[22] Filed: Aug. 8, 1991

Related U.S. Application Data

[63] Continuation-in-part of Ser. No. 641,343, Jan. 17, 1991, abandoned.

[51] Int. Cl.⁶ .................... A61K 37/00; C07K 7/00
[52] U.S. Cl. .................................... 530/308
[58] Field of Search ................ 435/69.1, 69.4; 530/308

[56] References Cited

FOREIGN PATENT DOCUMENTS 0189998  8/1986  European Pat. Off. .
8809341 12/1988  WIPO .
WO92/12998 8/1992 WIPO .

OTHER PUBLICATIONS

Zuranski et al EMBO vol. 8 No. 9 pp. 2583–2590 Sep. 1989.
Gysin et al. Biochemistry vol. 25 pp. 8278–8284, 1986.
Merrifield, R. B. et al., "Synthetic Peptide Antagonists of Glucagon," in Theodoropoulos (ed.), Peptides 1986. *Proceedings of the 19th European Peptide Symposium* (Chilkidiki, Greece) Walter de Gruyte, New York, 1987, pp. 517–520.

*Primary Examiner*—Robert A. Wax
*Assistant Examiner*—David Schmickel
*Attorney, Agent, or Firm*—Seed and Berry

[57] ABSTRACT

Methods for detecting glucagon antagonists through the use of recombinant DNA techniques are provided. Briefly, subsequent to the expression of glucagon analogs within suitable host cells, the analogs are exposed to a glucagon receptor coupled to a response pathway in the presence of native glucagon. A reduction in the stimulation of the response pathway resulting from the binding of the glucagon analog to the glucagon receptor relative to the stimulation of the response pathway by native glucagon alone indicates the presence of a glucagon antagonist. Glucagon antagonists identified and isolated through the methods are also provided.

3 Claims, 4 Drawing Sheets

Sequence ID Numbers 1 and 2

```
1           10          20          30          40
CAC TCT CAA GGT ACC TTT ACC TCT GAC TAC TCT AAG TAT CTA GAC TCG
His Ser Gln Gly Thr Phe Thr Ser Asp Tyr Ser Lys Tyr Leu Asp Ser 50          60          70          80
AGG CGT GCT CAA GAC TTT GTT CAA TGG TTG ATG AAT ACC
Arg Arg Ala Gln Asp Phe Val Gln Trp Leu Met Asn Thr
```

Fig. 3

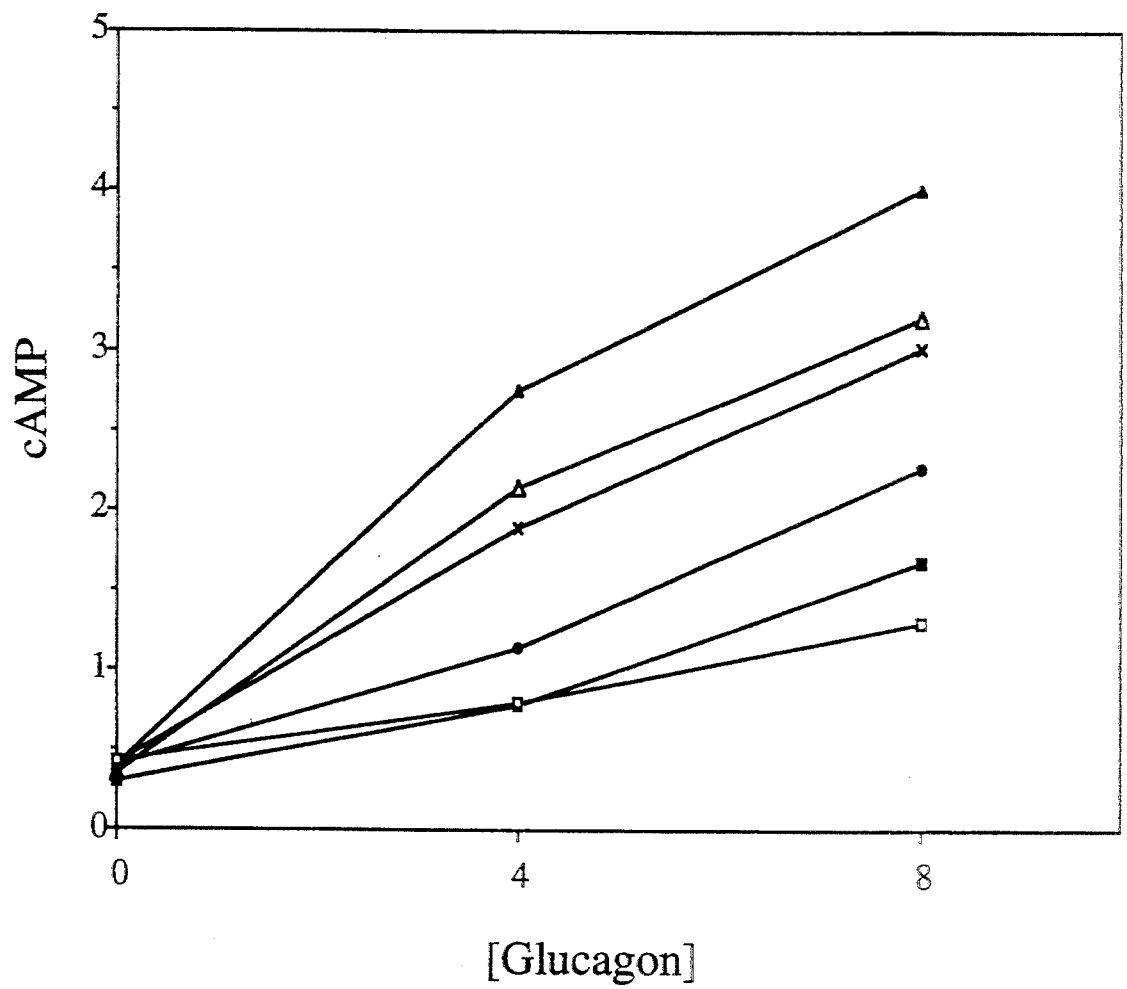
FIGURE 4: cAMP Response Curves Selected mutants and controls

METHODS FOR DETECTING GLUCAGON ANTAGONISTS

CROSS-REFERENCE TO RELATED APPLICATION

This application is a continuation-in-part to U.S. patent application Ser. No. 07/641,343, filed Jan. 17, 1991, now abandoned.

TECHNICAL FIELD

The present invention is directed generally toward methods for detecting glucagon antagonists, and more specifically, to methods of producing and screening large numbers of potential glucagon antagonists through the use of recombinant DNA techniques.

BACKGROUND OF THE INVENTION

Human diabetes, a disease in which a major indicator is an elevated blood glucose level, is generally believed to result from low insulin levels and elevated glucagon levels. However, hyperglycemia in non-insulin dependent diabetes, in both non-obese and obese patients, has been shown in the presence of both elevated glucagon and insulin levels.

Insulin is known to rapidly decrease blood glucose levels while glucagon, a polypeptide hormone twenty-nine amino acid residues in length, is believed to contribute to elevated blood glucose levels by binding to liver membrane receptors, and thereby triggering glycogenolysis, which results in the production of glucose. Elevated glucagon levels are also associated with a substantial increase in gluconeogenesis.

While stable control of insulin levels is difficult to achieve, treatment for insulin-dependent diabetes and some non-insulin dependent diabetes has been achieved through a combination of controlled diet and periodic doses of exogenous insulin. It is believed that the therapeutic use of glucagon antagonists will inhibit glycogenolysis and help to lower blood glucose levels in diabetics. These antagonists have the ability to bind to the glucagon receptor in the liver membrane, but are incapable of stimulating adenylate cyclase activity. The binding of glucagon to its cellular receptor is believed to trigger the stimulation of adenylate cyclase activity resulting in the production of cyclic AMP (cAMP), and results in an increase in glycogenolysis and its accompanying release of glucose.

Current methods for developing glucagon antagonists have relied on the development of specific glucagon analogs through the deletion or substitution of specific amino acids using solid-phase peptide synthesis, and high-level purification of these glucagon analogs through solid-phase synthesis methods and associated chromatographic methods. See, for example, Unson et al. (*Peptides* 10:1171–1178, 1989) Andreu and Merrifield (*Eur. J. Biochem.* 164:585–590, 1987), Gysin et al. (*Biochemistry* 25:8278–8284, 1986), Merrifield (U.S. Pat. No. 4,879,273) and Hruby (U.S. Pat. No. 4,430,326). These methods, however, do not lend themselves to the high through-put screening of large numbers of glucagon analogs.

There exists a need in the art for a method of detecting glucagon antagonists that does not rely upon the high-purity, solid-phase synthesis of glucagon analogs. The present method, through the use of recombinant DNA methods, permits the production of high numbers of glucagon analogs for screening through high through-put antagonist screening assays.

DISCLOSURE OF INVENTION

Briefly stated, the present invention provides methods for detecting the presence of glucagon antagonists. In one aspect, the method comprises: (a) growing host cells containing a DNA construct capable of directing the expression of glucagon analogs, the construct comprising the following operably linked elements: a transcriptional promoter, a secretory signal sequence, a DNA sequence encoding a glucagon analog and a transcriptional terminator, under growth conditions suitable for the expression of the glucagon analog; (b) isolating the glucagon analog encoded by the DNA sequence from the host cells; (c) exposing the isolated glucagon analog in the presence of native glucagon to a glucagon receptor coupled to a response pathway under conditions and for a time sufficient to allow binding of the glucagon analog to the receptor and an associated response through the pathway; and (d) detecting a reduction in the stimulation of the response pathway resulting from the binding of the glucagon analog to the glucagon receptor, relative to the stimulation of the response pathway by native glucagon alone and therefrom determining the presence of a glucagon antagonist.

Within a related aspect, the method comprises: (a) growing a pool of host cells, each containing a DNA construct capable of directing the expression of a glucagon analog and comprising the following operably linked elements: a transcriptional promoter, a secretory signal sequence, a DNA sequence encoding a glucagon analog and a transcriptional terminator, under growth conditions suitable for the expression of the glucagon analogs; (b) isolating the glucagon analogs encoded by the DNA sequences from the host cells; (c) exposing the isolated glucagon analogs in the presence of native glucagon to a glucagon receptor coupled to a response pathway under conditions and for a time sufficient to allow binding of the glucagon analog to the receptor and an associated response through the pathway; and (d) detecting a reduction in the stimulation of the response pathway resulting from the binding of the glucagon analog to the glucagon receptor relative to the stimulation of the response pathway by native glucagon alone and therefrom determining the presence of a glucagon antagonist.

Within another aspect of the present invention, glucagon antagonists are produced from a host cell containing a DNA construct capable of directing the expression of a glucagon antagonist, the construct comprising the following operably linked elements: a transcriptional promoter, a secretory signal sequence, a DNA sequence encoding a glucagon antagonist, wherein the sequence encodes one or more amino acid residues that are different than the corresponding amino acid residues in native glucagon, and a transcriptional terminator.

These and other aspects will become evident upon reference to the following detailed description and attached drawings.

Figure 1:
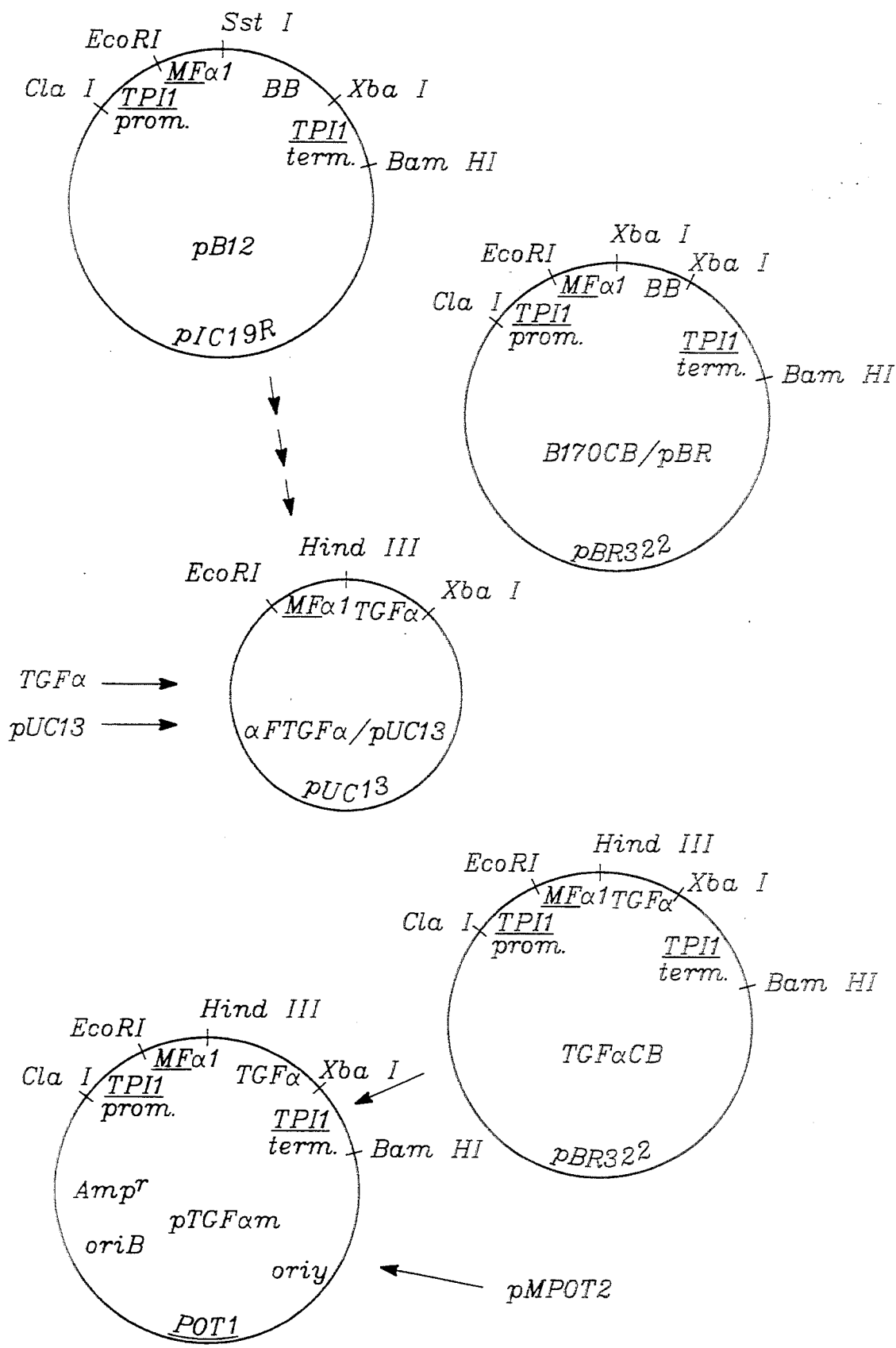
FIG. 1 illustrates the subcloning of the *S. cerevisiae* TPI1 promoter and alpha factor prepro sequences.

FIG. 3 discloses a native glucagon coding sequence corresponding to sequence ID Nos. 1 and 2, which was used for the base sequence for the synthesis of the glucagon and des-His[1]-glucagon oligonucleotide libraries. Numbers above the line refer to the nucleotide sequence.

FIG. 4 discloses cAMP response curves of rat liver membranes to three concentrations of glucagon in the presence of representative glucagon analogs relative to the controls des-His[1]-glucagon and des-His[1]-[Glu[9]]-glucagon.

DETAILED DESCRIPTION OF THE INVENTION

Prior to setting forth the invention, it may be helpful to an understanding thereof to set forth definitions of certain terms to be used hereinafter.

Analog: A molecule, other than a native ligand, capable of being bound by the ligand-binding domain of a receptor. The molecule may be chemically synthesized, produced through recombinant DNA methodology or may occur in nature.

As used herein, glucagon analogs are glucagon-like polypeptides which contain one or more amino acid residues that are different than the corresponding amino acid residues in native glucagon and are capable of binding to a glucagon receptor. These differences may comprise deletions, additions and/or substitutions of amino acids relative to native glucagon.

Response pathway: A response pathway is a biochemical pathway activated in response to external stimuli that is generally but not always directly coupled to a membrane-bound receptor. Response pathways generally induce cellular responses such as extracellular matrix secretion from responsive cell lines, hormone secretion, chemotaxis, differentiation, or the inhibition of cell division of responsive cells. One such response pathway is the adenylate cyclase response pathway, which is coupled to the membrane-bound glucagon receptor. The adenylate cyclase response pathway is induced upon binding of glucagon to its cellular receptor, thereby producing increased intracellular concentrations of cyclic AMP (cAMP).

Antagonist: A molecule capable of binding to a receptor, but that does not stimulate or exhibits reduced stimulation of a response pathway within a cell. Glucagon antagonists are generally identified by their ability to bind to the glucagon receptor and their inability to stimulate a cellular response pathway. In general, putative glucagon antagonists are combined with native glucagon and the production of cAMP is assayed in an adenylate cyclase assay. Glucagon antagonists are identified as those molecules that reduce the stimulation of cAMP production relative to native glucagon alone.

DNA Construct: A DNA molecule, or a clone of such a molecule, either single- or double-stranded that has been modified through human intervention to contain segments of DNA combined and juxtaposed in a manner that as a whole would not otherwise exist in nature.

DNA constructs contain the information necessary to direct the expression, and preferably the secretion of DNA sequences encoding polypeptides of interest. Such DNA constructs, known as expression vectors, will generally include promoters, enhancers and transcription terminators. DNA constructs containing the information necessary to direct the secretion of a polypeptide will also contain at least one secretory signal sequence.

Secretory Signal Sequence: A DNA sequence encoding a secretory peptide. A secretory peptide is an amino acid sequence that acts to direct the secretion of a mature polypeptide or protein from a cell. Secretory peptides are characterized by a core of hydrophobic amino acids and are typically (but not exclusively) found at the amino termini of newly synthesized proteins. Very often the secretory peptide is cleaved from the mature protein during secretion. Such secretory peptides contain processing sites that allow cleavage of the signal peptides from the mature protein as it passes through the secretory pathway. Processing sites may be encoded within the signal peptide or may be added to the signal peptide by, for example, in vitro mutagenesis. Certain secretory peptides may be used in concert to direct the secretion of polypeptides and proteins. One such secretory peptide that may be used in combination with other secretory peptides is the third domain of the yeast Barrier protein.

As noted above, an object of the present invention is to provide improved methods for detecting glucagon antagonists using recombinant methods and host cells. The present invention provides the ability to produce glucagon analogs from transformed or transfected host cells. The analogs are exposed, in the presence of native glucagon, to a glucagon receptor coupled to a response pathway. A reduction in the stimulation of the response pathway as compared to the stimulation obtained using native glucagon alone is indicative of the presence of a glucagon antagonist. Within the present invention, it is preferred that the reduction in the stimulation of the response pathway be equivalent to or greater than the reduction associated with des-His[1]-glucagon, as discussed in more detail below. Glucagon analogs produced according to the present invention may be screened in high throughput antagonist screens. By using recombinant DNA methods, the present invention also provides a method for screening pools of glucagon analogs within such high through-put screens to identify glucagon antagonists. The present invention also provides methods for producing glucagon antagonists through the use of recombinant host cells.

The present invention provides methods for producing large numbers of glucagon analogs using pools of DNA sequences encoding such analogs. Glucagon coding sequences may be produced synthetically using standard techniques or may be cloned from, for example, pancreatic cells, using standard cloning methods such as those described by Maniatis et al. (*Molecular Cloning: A Laboratory Manual*, Cold Spring Harbor, N.Y., 1982; which is incorporated herein by reference) or Sambrook et al. (*Molecular Cloning: A Laboratory Manual, Second Edition*, Cold Spring Harbor, N.Y., 1989; which is incorporated herein by reference). Glucagon cDNAs have been isolated by, for example, Lund et al. (*Proc. Natl. Acad. Sci. USA* 79:345–349, 1982), Bell et al. (*Nature* 302:716–718, 1983), Lopez et al. (*Proc. Natl. Acad. Sci. USA* 80:5485–5489, 1983), Bell et al. (*Nature* 704:368–371, 1983) and Heinrich et al. (*J. Biol. Chem*, 259:14082–14087, 1984). Pools of DNA sequences encoding glucagon analogs may be generated by saturation mutagenesis of a DNA sequence encoding glucagon (using, for example, the methods described by Little (*Gene* 88:113–115, 1990), or Hermes et al. (Gene 88:143–151, 1989), or segment-directed mutagenesis (as described, for example, by Shortle et al., *Proc. Natl. Acad. Sci. USA* 77:5375-5379, 1980). Alternatively, pools of glucagon analogs may be generated by forced nucleotide misincorporation as described by, for example, Liao and Wise (*Gene* 88:107-111, 1990). Briefly, Liao and Wise describe a method for introducing random point mutations into a cloned DNA fragment via the forced misincorporation of deoxynucleoside triphosphates by either a reverse transcriptase or a mutant T7 DNA polymerase. In combination with specific primers and limiting amounts of non-mutagenic nucleoside triphosphates, these two polymerases, which lack proofreading activity, result in the incorporation of incorrect nucleotides into the primed sequence and provide a wide spectrum of random mutations in a given sequence. Preferably, pools of DNA sequences encoding glucagon analogs are generated by synthesizing randomly mutagenized oligonucleotides using, for example, the method described by Hutchinson et al. (*Proc. Natl. Acad. Sci. USA* 83:710-714, 1986). Preferably, oligonucleotides encoding glucagon analogs are synthesized to form adapters upon hybridization such that the glucagon analog coding sequence is flanked by adhesive ends. It may be particularly preferred to add a sequence encoding a bridging region which allows the in-frame fusion of sequences encoding a secretory signal sequence and the glucagon coding sequence. It may also be particularly preferred to synthesize DNA sequences that encode des-His[1]-glucagon analogs (lacking the codon corresponding to the first amino acid residue of mature glucagon). DNA sequences encoding glucagon analogs are preferably synthesized on an oligonucleotide synthesizer by cross contaminating the reagent bottles that normally contain pure phosphoramidites corresponding to the bases A, G, C, and T at low levels with each of the other bases. Cross contamination of the reagent bottles may be achieved by adding between 0.01% and 14% of each incorrect base, with a cross contamination of between 0.8% and 2% being preferred, and 1% being particularly preferred. The synthesis of the oligonucleotides from a single non-mutagenized residue is particularly preferred. A 1% cross contamination with each incorrect base will theoretically lead to approximately 2.5 base changes per molecule.

The oligonucleotides encoding glucagon analogs are annealed with mutagenized or non-mutagenized oligonucleotides encoding either native or des-His[1]-glucagon. Pools of the annealed oligonucleotide adapters encoding glucagon analogs or des-His[1]-glucagon analogs may be inserted into a suitable expression vector which is in turn introduced by transfection or transformation into a suitable eukaryotic host cell. Expression vectors for use in carrying out the present invention will comprise a promoter capable of directing the transcription of a cloned DNA and a transcriptional terminator.

To direct proteins of the present invention into the secretory pathway of the host cell, at least one secretory signal sequence is operably linked to the DNA sequence of interest. Preferred secretory signals include the glucagon secretory signal (pre-pro sequence), the alpha factor signal sequence (pre-pro sequence; Kurjan and Herskowitz, *Cell* 30:933-943, 1982; Kurjan et al., U.S. Pat. No. 4,546,082; Brake, EP 116,201), the PHO5 signal sequence (Beck et al., WO 86/00637), the BAR1 secretory signal sequence (MacKay et al., U.S. Pat. No. 4,613,572; MacKay, WO 87/002670), the SUC2 signal sequence (Carlson et al., *Mol. Cell. Biol.* 3:439-447, 1983), the α-1-antitrypsin signal sequence (Kurachi et al., *Proc,. Natl. Acad. Sci. USA* 78:6826-6830, 1981), the α-2 plasmin inhibitor signal sequence (Tone et al., *J. Biochem. (Tokyo)* 102:1033-1042, 1987), the tissue plasminogen activator signal sequence (Pennica et al., *Nature* 301:214-221, 1983), the *E. coli* PhoA signal sequence (Yuan et al., *J. Biol. Chem.* 265:13528-13552, 1990) or any of the bacterial signal sequences reviewed, for example, by Oliver (*Ann. Rev. Microbiol.* 39:615-649, 1985). Alternatively, a secretory signal sequence may be synthesized according to the rules established, for example, by Von Heinje (*Eur. J. Biochem.* 133:17-21, 1983; *J. Mol. Biol.* 184:99-105, 1985; *Nuc. Acids Res.* 14:4683-4690, 1986).

Secretory signal sequences may be used singly or may be combined. For example, a first secretory signal sequence may be used singly or in combination with a sequence encoding the third domain of Barrier (described in co-pending commonly assigned U.S. patent application Ser. No. 07/270,933, which is incorporated by reference herein in its entirety). The third domain of Barrier may be positioned in proper reading frame 3' of the DNA sequence of interest or 5' to the DNA sequence and in proper reading frame with both the secretory signal sequence and the DNA sequence of interest.

Host cells for use in practicing the present invention include mammalian, avian, plant, insect, bacterial and fungal cells. Fungal cells, including species of yeast (e.g., Saccharomyces spp., Schizosaccharomyces spp.) or filamentous fungi (e.g., Aspergillus spp., Neurospora spp.) may be used as host cells within the present invention. Strains of the yeast *Saccharomyces cerevisiae* are particularly preferred.

Suitable yeast vectors for use in the present invention include YRp7 (Struhl et al., *Proc. Natl. Acad, Sci,. USA* 76:1035-1039, 1978), YEp13 (Broach et al., *Gene* 8:121-133, 1979), POT vectors (Kawasaki et al, U.S. Pat. No. 4,931,373, which is incorporated by reference herein), pJDB249 and pJDB219 (Beggs, *Nature* 275:104-108, 1978) and derivatives thereof. Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al., ibid.), URA3 (Botstein et al., *Gene* 8:17, 1979), HIS3 (Struhl et al., ibid.) or POT1 (Kawasaki et al., ibid.). Another suitable selectable marker is the CAT gene, which confers chloramphenicol resistance on yeast cells.

Preferred promoters for use in yeast include promoters from yeast glycolytic genes (Hitzeman et al., *J. Biol. Chem.* 255:12073-12080, 1980; Alber and Kawasaki, *J. Mol. Appl. Genet.* 1:419-434, 1982; Kawasaki, U.S. Pat. No. 4,599,311) or alcohol dehydrogenase genes (Young et al., in *Genetic Engineering of Microorganisms for Chemicals*, Hollaender et al., (eds.), p. 355, Plenum, New York, 1982; Ammerer, *Meth. Enzymol.* 101:192-201, 1983). In this regard, particularly preferred promoters are the TPI1 promoter (Kawasaki, U.S. Pat. No. 4,599,311, 1986) and the ADH2-4[c] promoter (Russell et al., *Nature* 304:652-654, 1983; Irani and Kilgore, U.S. patent application Ser. No. 183,130, which is incorporated herein by reference). The expression units may also include a transcriptional terminator.

A preferred transcriptional terminator is the TPI1 terminator (Alber and Kawasaki, ibid.).

In addition to yeast, proteins of the present invention can be expressed in filamentous fungi, for example, strains of the fungi Aspergillus (McKnight et al., U.S. Pat. No. 4,935,349, which is incorporated herein by reference). Examples of useful promoters include those derived from *Aspergillus nidulans* glycolytic genes, such as the ADH3. promoter (McKnight et al., *EMBO J.* 4:2093-2099, 1985) and the tpiA promoter. An example of a suitable terminator is the ADH3 terminator (McKnight et al., ibid., 1985). The expression units utilizing such components are cloned into vectors that are capable of insertion into the chromosomal DNA of Aspergillus.

Techniques for transforming fungi are well known in the literature, and have been described, for instance, by Beggs (ibid.), Hinnen et al. (*Proc. Natl. Acad. Sci. USA* 75:1929-1933, 1978), Yelton et al. (*Proc. Natl. Acad. Sci. USA* 81:1740-1747, 1984), and Russell (*Nature* 301:167-169, 1983). The genotype of the host cell will generally contain a genetic defect that is complemented by the selectable marker present on the expression vector. Choice of a particular host and selectable marker is well within the level of ordinary skill in the art. To optimize production of the heterologous proteins, it is preferred that the host strain carries a mutation, such as the yeast pep4 mutation (Jones, *Genetics* 85:23-33, 1977), which results in reduced proteolytic activity.

In addition to fungal cells, cultured mammalian cells may be used as host cells within the present invention. Preferred cultured mammalian cells for use in the present invention include the COS-1 (ATCC CRL 1650), BHK, and 293 (ATCC CRL 1573; Graham et al., *J. Gen. Virol.* 36:59-72, 1977) cell lines. A preferred BHK cell line is the BHK 570 cell line (deposited with the American Type Culture Collection under accession number CRL 10314). In addition, a number of other mammalian cell lines may be used within the present invention, including Rat Hep I (ATCC CRL 1600), Rat Hep II (ATCC CRL 1548), TCMK (ATCC CCL 139), Human lung (ATCC CCL 75.1), Human hepatoma (ATCC HTB-52), Hep G2 (ATCC HB 8065), Mouse liver (ATCC CCL 29.1), NCTC 1469 (ATCC CCL 9.1) and DUKX cells (Urlaub and Chasin, *Proc. Natl. Acad. Sci USA* 77:4216-4220, 1980).

Mammalian expression vectors for use in carrying out the present invention will include a promoter capable of directing the transcription of a cloned gene or cDNA. Preferred promoters include vital promoters and cellular promoters. Viral promoters include the immediate early cytomegalovirus promoter (Boshart et al., *Cell* 41:521-530, 1985) and the SV40 promoter (Subramani et al., *Mol. Cell. Biol.* 1:854-864, 1981). Cellular promoters include the mouse metallothionein-1 promoter (Palmiter et al., U.S. Pat. No. 4,579,821), a mouse $V_\kappa$ promoter (Bergman et al., *Proc. Natl. Acad. Sci. USA* 81:7041-7045, 1983; Grant et al., *Nuc. Acids Res.* 15:5496, 1987) and a mouse $V_H$ promoter (Lob et al., *Cell* 33:85-93, 1983). A particularly preferred promoter is the major late promoter from Adenovirus 2 (Kaufman and Sharp, *Mol. Cell. Biol.* 2:1304-13199, 1982). Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Suitable polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nuc. Acids Res.* 9:3719-3730, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer and the mouse $\mu$ enhancer (Gillies, *Cell* 33:717-728, 1983). Expression vectors may also include sequences encoding the adenovirus VA RNAs.

Cloned DNA sequences may be introduced into cultured mammalian cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973.) Other techniques for introducing cloned DNA sequences into mammalian cells, such as electroporation (Neumann et al., *EMBO J.* 1:841-845, 1982), may also be used. In order to identify cells that have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. A preferred amplifiable selectable marker is the DHFR gene. Selectable markers are reviewed by Thilly (*Mammalian Cell Technology*, Butterworth Publishers, Stoneham, Mass., which is incorporated herein by reference). The choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA" to the mixture which is introduced into the cells.

Transfected mammalian cells are allowed to grow for a period of time, typically 1-2 days, to begin expressing the DNA sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels.

Preferred prokaryotic host cells for use in carrying out the present invention are strains of the bacteria *Escherichia coli*, although Bacillus and other genera are also useful. Techniques for transforming these hosts and expressing foreign DNA sequences cloned therein are well known in the art (see, e.g., Maniatis et al., *Molecular cloning: A Laboratory Manual*, Cold Spring Harbor Laboratory, 1982; which is incorporated herein by reference, or Sambrook et al., *Molecular Cloning: A Laboratory Manual, Second Edition*, Cold Spring Harbor, N.Y., 1989; which is incorporated herein by reference). Vectors used for expressing cloned DNA sequences in bacterial hosts will generally contain a selectable marker, such as a gene for antibiotic resistance, and a promoter that functions in the host cell. Appropriate promoters include the trp (Nichols and Yanofsky, *Meth. Enzymol.* 101:155–164, 1983), lac (Casadaban et al., *J. Bacteriol.* 143:971–980, 1980), and phage λ (Queen, *J. Mol. Appl. Genet.* 2:1–10, 1983) promoter systems. Plasmids useful for transforming bacteria include pBR322 (Bolivar et al., *Gene* 2:95–113, 1977), the pUC plasmids (Messing, *Meth. Enzymol.* 101:20–78, 1983; Vieira and Messing, *Gene* 19:259–268, 1982), pCQV2 (Queen, ibid.), and derivatives thereof. Plasmids may contain both viral and bacterial elements.

Given the teachings provided herein, promoters, terminators and methods for introducing expression vectors encoding glucagon analogs of the present invention into plant, avian and insect cells would be evident to those of skill in the art. The use of baculoviruses, for example, as vectors for expressing heterologous DNA sequences in insect cells has been reviewed by Atkinson et al. (*Pestic. Sci.* 28:215–224, 1990). The use of *Agrobacterium rhizogenes* as vectors for expressing genes in plant cells has been reviewed by Sinkar et al. (*J. Biosci..(Bangalore)* 11:47–58, 1987).

Host cells containing DNA constructs of the present invention are then grown to produce the glucagon analogs of the present invention. The cells are grown according to standard methods in a growth medium containing nutrients required for growth of mammalian or fungal host cells. A variety of suitable media are known in the art and generally include a carbon source, a nitrogen source, essential amino acids, vitamins, minerals and growth factors. The growth medium will generally select for cells containing the DNA construct by, for example, drug selection or deficiency in an essential nutrient which is complemented by the selectable marker on the DNA construct or co-transfected with the DNA construct.

Suitable growth conditions for yeast cells, for example, include culturing in a chemically defined medium, comprising a nitrogen source, which may be a non-amino acid nitrogen source or a yeast extract, inorganic salts, vitamins and essential amino acid supplements at a temperature between 4° C. and 37° C., with 30° C. being particularly preferred. The pH of the medium is preferably maintained at a pH greater than 2 and less than 8, more preferably pH 5–6. Methods for maintaining a stable pH include buffering and constant pH control, preferably through the addition of sodium hydroxide. Preferred buffering agents include succinic acid and Bis-Tris (Sigma Chemical Co., St. Louis, Mo.). Yeast cells having a defect in a gene required for asparagine-linked glycosylation are preferably grown in a medium containing an osmotic stabilizer. A preferred osmotic stabilizer is sorbitol supplemented into the medium at a concentration between 0.1M and 1.5M, preferably at 0.5M or 1.0M. Cultured mammalian cells are generally cultured in commercially available serum-containing or serum-free media. Selection of a medium appropriate for the particular cell line used and suitable growth conditions is within the level of ordinary skill in the art.

Individual transformants expressing the glucagon analogs may then be cloned or pooled as discussed herein. In the case of *Saccharomyces cerevisiae* transformants, individual transformants may be picked using sterile toothpicks onto selective media. In the case of cultured mammalian cell transfectants, individual transfectants may be isolated by cylinder cloning into multi-well culture plates. These assays will generally include the steps of (a) growing host cells containing a DNA construct capable of directing the expression of a glucagon analog, the construct comprising the following operably linked elements: a transcriptional promoter, a secretory signal sequence, a DNA sequence encoding a glucagon analog and a transcriptional terminator, under growth conditions suitable for the expression of the glucagon analog; (b) isolating the glucagon analog encoded by the DNA sequence from the host cells; (c) exposing the isolated glucagon analogs in the presence of native glucagon to a glucagon receptor coupled to a response pathway under conditions and for a time sufficient to allow binding of the glucagon analog to the receptor and an associated response through the pathway; (d) detecting a reduction in the stimulation of the response pathway resulting from the binding of the glucagon analog to the glucagon receptor relative to the stimulation of the response pathway by native glucagon, and therefrom determining the presence of a glucagon antagonist. Conditions and times sufficient for the binding of the glucagon analog to the receptor will vary with the source of the receptor; however, conditions suitable for the binding will generally be between 4° C. and 55° C. in a buffer solution between 0 and 2M NaCl, preferably between 0 and 0.9M NaCl, with 0.1M NaCl being particularly preferred, within a pH range of between 5 and 9, preferably between 6.8 and 8. Sufficient time for the binding and response will generally be between 5 and 15 minutes after exposure, with 12 minutes being particularly preferred.

As noted above, antagonists are capable of binding to a cellular receptor of the native molecule, but either are incapable of stimulating a response pathway or exhibit reduced stimulation of a response pathway. In one embodiment, glucagon antagonists have generally been identified through their ability to bind to a cellular glucagon receptor and their inability to stimulate the adenylate cyclase response pathway. Glucagon receptors have been reported in a number of tissues, for example, liver, kidney, cardiac muscle and adipose tissue from a number of species including dog, pig, human and rat. Adenylate cyclase activity assays may be carried out using, for example, the method described by Lin et al. (*Biochemistry* 14:1559–1563, 1975). These methods measure the level of stimulation of cAMP production relative to native glucagon and generally involve exposing a membrane preparation from tissue containing glucagon receptors to a mixture of glucagon and the glucagon analog in the presence of ATP. Membrane preparations from rat liver are generally used for adenylate cyclase activity assays although other tissues containing glucagon receptors may be used. Membranes may be prepared using the method described by Neville (*Biochim. Biophys Acta* 154:540–552, 1968) as modified by Pohl (*Methods in Receptor Research*, Ed. Blecher, M., New York, pp 160–164, 1976). Briefly, young female Sprague-Dawley rats were used for the preparation of the liver membranes; however, other laboratory strains are acceptable. Sixty to one hundred grams of rat liver are batch processed by first mincing the tissue into approximately 3–6 mm pieces. The minced tissue is suspended in ice cold 1 mM sodium bicarbonate at a concentration of approximately 300 g/l. The suspension is batch processed in a tissue homogenizer with eight strokes of the loose pestle. The homogenate is mixed with additional ice cold 1 mM sodium bicarbonate to yield a final concentration of about 40–80 g/l. The diluted homogenate is stirred for at least three minutes following which it is filtered through a double layer of cheese cloth. The filtrate is refiltered through four layers of cheese cloth and transferred to centrifuge bottles and centrifuged at 1500×g for 30 minutes at 4° C.

After centrifugation, the supernatant is carefully decanted and discarded, and the pellets are gently resuspended in the remaining supernatant with three strokes of the loose pestle in a clean tissue homogenizer. The volume of the resuspended supernatant is to total 165 ml in a final concentration of 44% sucrose. After thorough mixing, the sucrose concentration is measured with a refractometer and adjusted to between 43.9% to 44.1% sucrose (corresponding to a refractive index between 1.4076 and 1.4080) with either 69% sucrose or water. The adjusted suspension is distributed into six 1"×3.5" cellulose nitrate tubes and the tubes are filled and balanced by overlaying with a fresh sucrose solution which had been adjusted to a concentration between 42.2% to 42.4% sucrose (corresponding to a refractive index between 1.4042 and 1.4046). The samples are centrifuged in a swinging bucket ultracentrifuge rotor appropriate to the tubes being used (e.g., Beckman SW28 or SW25.2; Beckman Instruments, Inc., Fullerton, Calif.) at 25,000 rpm for 150 minutes at 4° C.

The purified membranes are recovered as a layer floating at the top meniscus of the tubes by either scooping with a spoon-shaped spatula or removal by suction into a syringe through an 18-gauge needle. The membranes are resuspended in 10 ml of 1 mM bicarbonate by suction and expulsion from a 10-25 ml syringe through an 18-gauge or 20-gauge needle. Following resuspension, the membranes are washed by adding 60-80 ml of 1 mM bicarbonate and centrifugation at 15,000 rpm in a high speed centrifuge. The supernatants are discarded, and the pellets are resuspended in 1 mM bicarbonate and pooled to yield approximately 5-10 ml of concentrated hepatocyte membranes. The membrane preparation is aliquoted and stored frozen at −80° C. for up to six months.

The protein concentration of the membrane preparation is determined by diluting 10-20 μl of the membrane preparation 100-fold in 1M NaCl, 0.17M sodium phosphate (pH 7.0) buffer. The absorbance of this solution relative to the buffer is measured in 1-cm quartz cuvettes at 224 nm and 236.5 nm wave length in a UV spectrophotometer. Protein concentration is calculated according to the formula:

$$A_{224nm} - A_{236.5} = (mg/ml\ protein)(6.45)(100)$$

An adenylate cyclase activity assay is carried out by first preparing solutions of Solution A, Solution B, 100×glucagon stock, and Stop Mix. Solution A contains between 50 mM and 200 mM Tris HCl between pH 7.4 to 7.8, between 20 mM to 100 mM $MgCl_2$, and between 0.2% to 0.4% bovine serum albumin (BSA). It may be preferable to add between 2 and 8 mg/ml of creatine phosphokinase (Sigma Chemical Co., St. Louis, Mo.). Most preferably, Solution A contains 100 mM Tris HCl pH 7.6, 20 mM $MgCl_2$, 0.4% BSA, 4 mg/ml creatine phosphokinase. Solution B contains between 0.4 and 20 mM ATP, between 1.6 μM and 25 mM GTP, between 0 and 4 mM isobutyl-1-methyl-xanthine (IBMX) and between 2 and 8 mM EDTA. It may be preferable to add between 60 and 240 mM creatine phosphate (Sigma Chemical Co.). Most preferably, Solution B contains 4 mM ATP, 20 μM GTP, 4 mM IBMX, 4 mM EDTA, and 120 nM creatine phosphate. 100×glucagon solution contains 1 μM glucagon. Stop mix contains 100 mM acetic acid, 50 mM EDTA. Alternatively, the reactions may be stopped by heating the reaction in a boiling water bath for 5 minutes. Glucagon receptor-containing membrane preparations may be prepared using the method of Pohl et al. (ibid.), which has been described above.

The adenylate cyclase reaction, which converts ATP to cAMP, may be carried out by adding the isolated glucagon analogs to the wells of a microtiter plate at micromolar concentrations. Equal volumes of Solution A and Solution B are mixed and 50 μl of the mixture is added to each negative control well. Glucagon is added to the remaining Solution A+Solution B mixture to a final concentration of $1 \times 10^{-8}M$ from the 100×glucagon stock solution, and 50 μl of this solution is added to each well containing a glucagon analog. The membrane preparation is diluted with water to between 0.2 and 10 mg/ml, preferably 2 mg/ml protein, and 45 μl of the diluted membranes are added to each well to start the reaction. The reaction mixtures are incubated at room temperature for 12 minutes, and the reactions are stopped by the addition of 100 μl of Stop solution to each well. The reactions are clarified by centrifugation and stored at 4° C.

In general, cAMP production is measured by the conversion of $^{32}P$-ATP to cAMP. Cyclic AMP production may be measured using the method of Salomon et al. (Anal. Biochem. 58:541-548, 1976) or Krishna et al. (J. Pharmacol. Exp. Ther. 163:379, 1968), or may be measured using a commercially available kit from, for example, Amersham Corporation. However, it is preferred that cAMP production be measured using a Scintillation Proximity Assay manufactured by Amersham (Arlington Heights, Ill.). Using the manufacturers directions, the Amersham Scintillation Proximity Assay Kit is used to measure the production of cAMP by competition of iodinated-cAMP with anti-cAMP antibodies. Preferably, 10 μl from each well of the adenylate cyclase reaction is added to individual beta plate wells and each sample is diluted with 65 μl of NaAcetate. Standards are prepared at 1.6 pM and 6.4 pM from the non-acetylation standards supplied with the Amersham kit and 75 μl of each standard is added to triplicate sample wells. One hundred-fifty microliters of buffer (Amersham) is added to triplicate wells for nonspecific binding controls. Seventy-five microliters of $^{125}I$-cAMP is added to each well. Seventy-five microliters of diluted rabbit anti-succinyl cAMP is added to each well, except the nonspecific binding control wells. Seventy-five microliters of diluted anti-rabbit SPA reagent is added to each well, and the plates sealed and incubated overnight at room temperature with shaking. After the overnight incubation, the reactions are counted in a beta-plate counter (Pharmacia, Uppsala, Sweden).

Within this embodiment, glucagon antagonists may be identified as those which inhibit the stimulation of the rat liver membrane adenylate cyclase by glucagon. The percent response may be determined using the formula:

$$\%R_X = (CPM - CPM_{NSB})/(CPM_{0.0} - CPM_{NSB})$$

where $\%R_X$=Percent response for a given sample or standard

CPM = Sample counts
$CPM_{NSB}$ = Mean NSB control counts
$CPM_{0.0}$ = Mean 0.0M standard counts
The relative concentration of cAMP for a given sample may be determined using the formula:

$$[cAMP]_X = 1.6 e^{ln4(\%Rx - \%R1.6)/(\%R6.4 - \%R1.6)}$$

where

[cAMP]$_x$ = the relative concentration of a given sample
%Rx = Percent response for a given sample
%R1.6 = Percent response for the $1.6 \times 10^{-9}$M standard
%R6.4 = Percent response for a the $6.4 \times 10^{-9}$M standard Thus, assay wells containing significantly less cAMP than the average may be identified as containing glucagon antagonists.

The glucagon antagonists of the present invention may be purified by ion-exchange and partition chromatography as described by, for example, Coy et al. (Peptides Structure and Function, Pierce Chemical Company, Rockford, Ill., pp. 369–372, 1983), by reverse-phase chromatography as described, for example, by Andreu and Merrifield (*Eur. J. Biochem*, 164:585–590, 1987), or by HPLC as described by, for example, Kofod et al., *Int. J. Peptide Protein Res.* 32:436–440, 1988). Additional purification may be achieved by conventional chemical purification means, such as liquid chromatography, gradient centrifugation, and gel electrophoresis, among others. Methods of protein purification are known in the art (see generally, Scopes, R., *Protein Purification*, Springer-Verlag, N.Y. (1982), which is incorporated herein by reference) and may be applied to the purification of the recombinant glucagon analogs described herein. Alternatively, glucagon analogs may be synthesized by the solid-phase method of Barany and Merrifield (in *The Peptides* Vol. 2A, Gross and Meienhofer, eds, Academic Press, N.Y., pp. 1–284, 1979) or by use of an automated peptide synthesizer.

Information obtained from glucagon antagonists produced through the mutagenesis or nucleotide misincorporation methods diclosed herein may be used to design additional glucagon antagonists. For example, data presented hereinbelow indicate that amino acid residues 1–5, 9, 11, 21 and 29 are important for glucagon activity. Changes at these positions may be combined to give a variety of glucagon antagonists, including des-His[1]-glucagons, that can be produced through genetic engineering techniques or by conventional chemical synthesis. Particularly preferred changes include the substitution of an alanine residue at position 11, a glutamate residue at position 21, and a serine residue at position 29.

Substantially pure recombinant glucagon antagonists of at least about 50% are preferred, at least about 70–80% more preferred, and 95–99% or more homogeneity most preferred, particularly for pharmaceutical uses. Once purified, partially or to homogeneity, as desired, the recombinant glucagon analogs may then be used therapeutically. In general, the antagonists of the present invention are administered parenterally or by infusion. The antagonists of the present invention may be present as free bases or as acid salts. Suitable salts will be pharmaceutically acceptable and include metal salts, alkali and alkaline earth metal salts such as potassium or sodium salts. Other pharmaceutically acceptable salts include citric, succinic, lactic, hydrochloric and hydrobromic acids. Parenteral compositions may be formulated in aqueous isotonic solutions of between pH 5.6 and 7.4. Suitable isotonic solutions include sodium chloride, dextrose, boric acid sodium tartrate, and propylene glycol solutions. Therapeutic doses of antagonists of the present invention may be administered simultaneously with insulin either in the same composition or in separate compositions.

The following examples are provided for purposes of illustration, not by way of limitation.

EXAMPLES

Example 1

Construction of the Yeast Expression Vector pBS114

Plasmid pEAS102, comprising portions of the yeast vectors YIp5 and pJDB207, was constructed as follows. Plasmid pJDB207 (Beggs, *Proceedings of Alfred Benzon Symposium* 16:383–389, "Molecular Genetics in Yeast," Copenhagen, Denmark, 1981), a derivative of pJDB219 (Beggs, ibid., 1978), was digested with Bam HI and Pst I to isolate the 4.4 kb fragment comprising the leu2-d gene, 2 micron plasmid and pBR322 sequences. Plasmid YIp5 (Struhl et al., ibid.) was subjected to partial digestion with Pst I and complete digestion with Bam HI to isolate the 4.3 kb fragment comprising the URA3 gene and pBR322 sequence. These two fragments were ligated and the resultant plasmid was designated pEAS102.

The Hind III site in plasmid pEAS102 was destroyed by first digesting pEAS102 with Hind III to completion. The linearized plasmid was then incubated with DNA polymerase I (Klenow fragment) in the presence of nucleotide triphosphates, recircularized by treatment with T4 DNA ligase and transformed into *E. coli* strain HB101. DNA prepared from the resulting transformants was screened for those plasmids which could no longer be linearized by digestion with Hind III.

To construct a yeast expression vector, the promoter and terminator regions from the *Saccharomyces cerevisiae* TPI1 gene along with the alpha factor (MFα1) prepro sequence were inserted into the pEAS102 derivative described above.

The TPI1 promoter and alpha factor prepro sequence were obtained plasmid pTGFαm (FIG. 1), which was derived from plasmid pB12, which contained the TPI1 promoter, the MFα1 prepro sequence, PDGF-BB sequence, the TPI1 terminator and pIC19R vector sequences. The construction of pB12 is described by Murray et al. (U.S. Pat. No. 4,766,073, which is incorporated herein by reference). The MFe1 prepro sequence and PDGF-BB sequence were subcloned as an Eco RI-Xba I fragment into M13. The Sst I site present in the MFα1 prepro sequence was changed to a Hind III site by in vitro mutagenesis using the method described by Kunkel et el. (U.S. Pat. No. 4,873,192) and oligonucleotide ZC1159 (Table 1, Sequence ID No. 3). A clone having a Hind III site in place of the Sst I site was identified. A fragment containing the MFα1 prepro sequence was isolated as an Eco RI-Hind III fragment.

TABLE 1

Oligonucleotide Sequences (5' to 3')

ZC1159 (Sequence ID Number 3)
TTG TCC AAG CTT ACA CCT TC

ZC1197 (Sequence ID Number 4)
AGC TTG GAC AAG AGA GTT GTT TCT CAC TTC AAC GAC TGT CCA
GAC CCT CAC ACC CAA TTC TGT TTC CAC GGT ACC TGT ACA T

ZC1198 (Sequence ID Number 5)
TCT TGG TTC AAG AAG ACA AGC CAG CAT GCG TTT GTC ACT CTG
GTT ACG TTG GTG CTA GAT GTG AAC ACG CTG TGT TGG CTT AAA T

ZC1199 (Sequence ID Number 6)
CCA ACA ATG TAC AGG TAC CGT GGA AAC AGA ATT GGG TGT GAG
AGT CTG GAC AGT CGT TGA AGT GAG AAA CAA CTC TCT TGT CCA

ZC1200 (Sequence ID Number 7)
CTA GAT TTA AGC CAA CAA GTC AGC GTG TTC ACA TCT AGC ACC
AAC GTA ACC AGA GTG ACA AAC GCA TGC TGG CTT GTC TTC TTG AA

ZC3020 (Sequence ID Number 8)
AGC TTA GAT AAG AGA CAC TCT CAA GGT ACC TTT ACC TCT GAC
TAC TCT AAG TAT CTA GAC TCG AGG CGT GCT CAA GAC TTT GTT
CAA TGG TTG ATG AAT ACC TGA ATT CA

ZC3021 (Sequence ID Number 9)
GAT CTG AAT TCA GGT ATT CAT CAA CCA TTG AAC AAA GTC TTG
AGC ACG CCT CGA GTC TAG ATA CTT AGA GTA GTC AGA GGT AAA
GGT ACC TTG AGA GTG TCT CTT ATC TA

ZC3378 (Sequence ID Number 10)
AGC TTA GAT AAG AGA TCT CAA GGT ACC TTT ACC TCT GAC TAC
TCT AAG TAT CTA GAC TCG AGG CGT GCT CAA GAC TTT GTT CAA
TGG TTG ATG AAT ACC TGA ATT CA

ZC3443 (Sequence ID Number 11)
GAT CTG AAT TCA GGT ATT CAT CAA CCA TTG AAC AAA GTC TTG
AGC ACG CCT CGA GTC TAG ATA CTT AGA GTA TTC AGA GGT AAA
GGT ACC TTG AGA TCT CTT ATC TA A transforming growth factor e (TGFα) sequence was synthesized using a set of four oligonucleotides designed and synthesized to form, when annealed, an adapter flanked on the 5' end with a Hind III adhesive end and on the 3' end with an Xba I adhesive end. Oligonucleotides ZC1197, ZC1198, ZC1199, and ZC1200 (Table 1, Sequence ID Nos. 4, 5, 6, and 7, respectively) were kinased, annealed and ligated into Xba I-Hind III linearized M13mp18. Single-stranded DNAs from the resultant clones were sequenced to confirm that the insert encoded TGFα. The TGFα insert was isolated as a Hind III-Xba I fragment.

As shown in FIG. 1, the Eco RI-Hind III fragment containing the MFα1 prepro sequence and the Hind III-Xba I fragment containing the TGFα sequence were ligated with Eco RI-Xba I linearized pUC13. The resultant plasmid, designated αfTGFα/pUC13, was digested with Eco RI and Xba I to isolate the MFα1-TGFα insert which was cloned into B170CB/pBR. Plasmid B170CB/pBR, which is described by Murray (U.S. patent application Ser. No. 07/557,219, which is incorporated herein by reference), contains the TPI1 promoter, MFα1 prepro sequence, PDGF-BB coding sequence, the TPI1 terminator and pBR322 vector sequences. Plasmid pB170CB/pBR was digested with Eco RI-Xba I to isolate the fragment containing the TPI1 promoter, pBR322 vector sequence and the TPI1 terminator. The Eco RI-Xba I pB170CB/pBR fragment and the Eco RI-Xba I MFα1-TGFα fragment were ligated. The resulting plasmid, designated TGFeCB, was digested with Cla I and Bam HI to isolate the expression unit, which was subcloned into the yeast expression vector pMPOT2 (a yeast 2 micron-based plasmid containing yeast and bacterial replication origins, ampicillin resistance gene and POT! selectable marker; deposited with American Type Culture Collection as an E. coli HB101 transformant under accession number 67788; disclosed by Murray et al., U.S. Pat. No. 4,766,073, incorporated herein by reference) to construct pTGFαm (FIG. 1). Plasmid pTGFαm was digested with Bgl II and Hind III to isolate the 1236 base pair fragment containing the TPI1 promoter and MFα1 prepro sequence.

The Saccharomyces cerevisiae TPI1 terminator fragment was obtained from plasmid pFG1 (Alber and Kawasaki, ibid.). It encompassed the region from the penultimate amino acid codon of the TPI1 gene to the Eco RI site approximately 700 base pairs downstream. A Bam HI site was substituted for the unique Eco RI site of pFG1 by first digesting the plasmid with Eco RI, then blunting the adhesive ends with DNA polymerase I (Klenow fragment), adding synthetic Bam HI linkers (CGGATCCA), and religating to produce plasmid p136. The TPI1 terminator was then excised from p136 as an Xba I-Bam HI fragment. This fragment was ligated into YEp13 (Broach et al., ibid.), which had been linearized with Xba I and Bam HI. The resulting plasmid was designated p213. The Hind III site was then removed from the TpI1 terminator region of p213 by digesting the plasmid with Hind III, blunting the resultant termini with DNA polymerase I (Klenow fragment), and recircularizing the linear molecule using T4

DNA ligase. The resulting plasmid was designated p270.

Alternatively, p270 may be constructed by digesting plasmid pM220 (deposited with American Type Culture Collection as an E. coli RR1 transformant, accession number 39853) with Xba I and Bam HI, purifying the TPI1 terminator fragment (approximately 700 bp) and inserting this fragment into Xba I-Bam HI digested YEp13.

The TPI1 terminator was removed from plasmid p270 as an Xba I-Bam HI fragment. This fragment was cloned into pUC19 along with another fragment containing the TPI 1 promoter joined to the CAT (chloramphenicol acetyl transferase) gene to obtain a TPI1 terminator fragment with an Eco RV end. The resultant plasmid was designated pCAT. The TPI1 terminator was then removed from pCAT as an Eco RV-Bam HI fragment and cloned into pIC19H (Marsh et al., ibid.), which had been linearized with the same enzymes, to obtain plasmid pTTI. Plasmid pTTI was then digested with Hind III and Sal I to isolate the 718 bp TPI1 terminator fragment.

Figure 2:
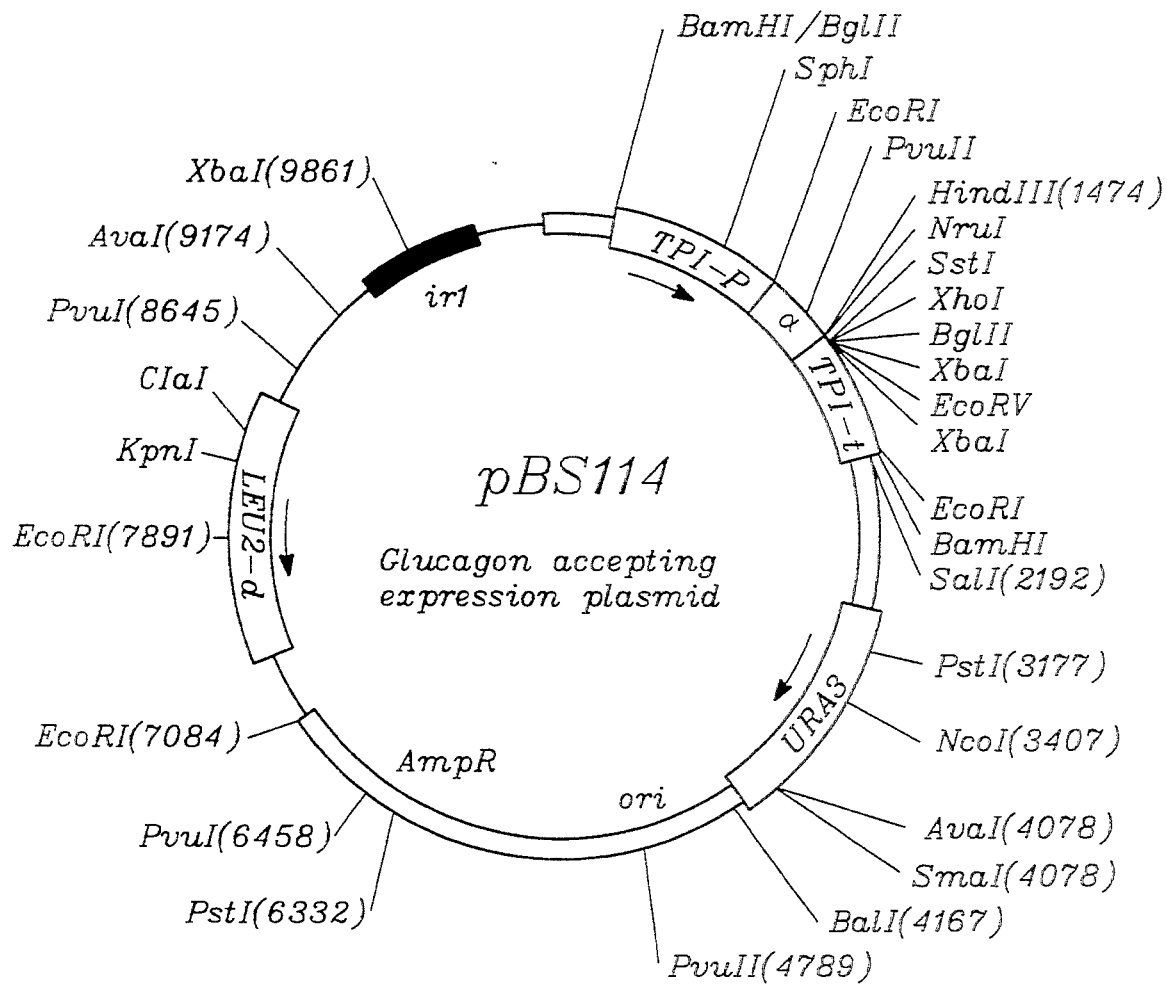
FIG. 2 discloses the representative expression vector pBS114. Abbreviations used include TPI-P, TPI1 promoter; α, alpha factor signal sequence; TPI-t, TPI1 terminator; and ir1, inverted repeat 1 of the 2 micron plasmid.

The 1236 base pair Bgl II-Hind III TPI1 promoter-MFα1 fragment and the 718 base pair Hind III-Sal I TPI1 terminator fragment were ligated with the pEAS102 derivative that have been linearized by digestion with Bam HI and Sal I. The ligation mixture was transformed into E. coli strain HB101, and plasmid DNA prepared from selected transformants was screened by restriction analysis to identify a clone bearing a plasmid of the correct structure. A positive clone was designated pBS114 (FIG. 2).

Example 2

Construction Of Control Expression Vectors Containing DNA Sequences Encoding Wild-Type Glucagon and Des-His$^1$-[Glu$^9$]-glucagon A. Construction of pBS117

A control expression plasmid was constructed which encoded a wild-type glucagon coding sequence. The glucagon coding sequence was designed to utilize codons found in highly expressed yeast genes, which would yield the greatest variety of amino acid replacements from single base changes, while excluding codons that were one base change away from the chain termination codons UAA, UAG and UGA. In addition, three restriction sites were designed into the sequence to allow confirmation of mutagenesis and to ease subsequent manipulations. This coding sequence (FIG. 3; Sequence ID No. 1) was used as the basis for the construction of both the glucagon analog oligonucleotide library and the des-His$^1$-glucagon oligonucleotide library.

The glucagon coding sequence was prepared from two synthetic oligonucleotides that were designed to provide, when annealed, a DNA sequence including a glucagon coding sequence as described above flanked by sequences that allow directional insertion into the expression vector such that the 5' end of the glucagon coding sequence is joined in frame to the alpha factor prepro sequence via a DNA segment encoding a KEX2 cleavage site. Oligonucleotides ZC3020 and ZC3021 (Table 1, Sequence ID Nos. 8 and 9) were designed to form, when annealed, an adapter encoding the amino acid sequence for wild type glucagon as described above, flanked on the 5' end with a Hind III adhesive end followed by a 15 base bridging sequence between the Hind III site and a KEX2 cleavage site sequence, and on the 3' end with a stop codon at the end of the glucagon sequence followed by an Eco RI site and a Bgl II adhesive end. Oligonucleotides ZC3020 and ZC3021 were annealed and ligated with pSB114, which had been linearized by digestion with Hind III and Bgl II. The resulting plasmid was designated pBS117. Plasmid pBS117 was transformed into *saccharomyces cerevisiae* strain ZY100 (ade2-101 leu2-3 leu2-112 ura3-52 suc2-D9 gal12 pep4::TPI1p-cAT) to create strain ZB210. Plasmid pBS114 was transformed into strain ZY100 to create strain ZB213 as a negative control. Transformants were initially selected on -URADS plates (Table 2). Individual transformant colonies were clonally purified by streaking on -LEUD plates (Table 2).

Table 2

Media Recipes

-LeuThrTrp Amino Acid Mixture
4 g adenine
3 g L-arginine
5 g L-aspartic acid
2 g L-histidine free base
6 g L-isoleucine
4 g L-lysine-mono hydrochloride
2 g L-methionine
6 g L-phenylalanine
5 g L-serine
5 g L-tyrosine
4 g uracil
6 g L-valine
Mix all the ingredients and grind with a mortar and pestle until the mixture is finely ground.

-UraThrTrp Amino Acid Mixture
4 g adenine
3 g L-arginine
5 g L-aspartic acid
2 g L-histidine free base
6 g L-isoleucine
6 6L-leucine
4 g L-lysine-mono hydrochloride
2 g L-methionine
6 g L-phenylalanine
5 g L-serine
5 g L-tyrosine
6 g L-valine
Mix all the ingredients and grind with a mortar and pestle until the mixture is finely ground.

-LEUD
20 g glucose
6.7 g Yeast Nitrogen Base without amino acids (DIFCO Laboratories Detroit, Mich.)
0.6 g -LeuThrTrp Amino Acid Mixture
18 g Agar
Mix all the ingredients in distilled water. Add distilled water to a final volume of 1 liter. Autoclave 15 minutes. After autoclaving add 150 mg L-threonine and 40 mg L-tryptophan. Pour plates and allow to solidify.

-LeuTrpThr Liquid Medium
20 g glucose
6.7 g Yeast Nitrogen Base without amino acids (DIFCO Laboratories Detroit, Mich.)
0.6 g -LeuThrTrp Amino Acid Mixture
Mix all the ingredients in distilled water. Add distilled water to a final volume of 1 liter. Autoclave 15 minutes. After autoclaving add 150 mg L-threonine and 40 mg L-tryptophan.

-URADS
20 g glucose
6.7 g Yeast Nitrogen Base without amino acids (DIFCO Laboratories Detroit, Mich.)
0.6 g -UraThrTrp Amino Acid Mixture
182.2 g sorbitol
18 g Agar Mix all the ingredients in distilled water. Add distilled water to a final volume of 1 liter. Autoclave 15 minutes. After autoclaving add 150 mg L-threonine and 40 mg L-tryptophan. Pour plates and allow to solidify.

Strains ZB210 and ZB213 were grown in -LeuTrpThr liquid medium for 40 hours at 30° C. The cultures were centrifuged for five minutes to clarify the spent media. The spent media were assayed as described in Example 5. When grown to moderate cell densities (2-6 g/l dry wt) culture medium from ZB210 was found to contain the equivalent of from 5-20 mg/ml glucagon as measured by radioimmuno assay.

B. Construction of Plasmid pBS120

A control expression plasmid which encoded a des-His$^1$-[Glu$^9$]glucagon coding sequence (described by Merrifield et al (ibid.)) was constructed from synthetic oligonucleotides. Oligonucleotides ZC3378 and ZC3443 (Table 1, Sequence ID Nos. 10 and 11) were designed to form a DNA sequence including a yeast codon-optimized des-His$^1$-[Glu$^9$]glucagon coding sequence flanked on the 5' end with a Hind III adhesive end followed by a 15 base bridging sequence between the Hind III site and a KEX2 cleavage site sequence, and on the 3' end with a stop codon at the end of the glucagon sequence followed by an Eco RI site and a Bgl II adhesive end. ZC3378 is a 107 base oligomer containing the coding sequence for unsubstituted des-His$^1$-glucagon and appropriate bridge sequences. ZC3443 is complementary to ZC3378 except for Hind III and Bgl II overhangs and a single base change in the codon for the aspartic acid residue normally found in position 9 of glucagon. Incorporation of this base change should result in a coding sequence for des-His$^1$-Glu$^9$]glucagon. Oligonucleotides ZC3378 and ZC3443 were annealed and ligated with Hind III-Bgl II linearized pBS114. Transformation of E. Coli HB101 with a ligation mix of ZC3378, ZC3443, and pBS114 yielded a mixture of plasmid clones, some encoding des-His$^1$-glucagon and some encoding des-His$^1$-[Glu$^9$]glucagon. One of the latter was identified by DNA sequencing and designated pBS120. Plasmid pBS120 was transformed into Saccharomyces cerevisiae strain ZY100 to create strain ZB216.

Example 3

Construction of a Glucagon Analog Oligonucleotide Library

A glucagon analog oligonucleotide library was constructed using an adaptation of the method described by Hutchinson et al. (ibid.). Briefly, oligonucleotides were synthesized using phosphoramidite solutions that had been purposely cross contaminated such that the solutions that normally contained the pure four phosphoramidite solutions corresponding to the bases A, G, C, and T were each contaminated with small amounts of phosphoramidites corresponding to all the bases. The cross contamination was performed by resuspending 1.0 g of each of the four phosphoramidites to a concentration of 0.13M by adding the following amounts of dry acetonitrile to sealed bottles: A, 11.8 ml; G, 12.1 ml; C 12.2 ml; and T, 13.7 ml. Three 0.17 ml aliquots were removed from each bottle in turn and were added to each of the other three reagents. Disallowing for the slight amount of back contamination caused by the sequential nature of this process (the bottles were swirled only after all transfers were made to minimize this phenomenon), the solutions were calculated to be 0.13M in total phosphoramidite concentration and had the compositions shown in Table 3.

TABLE 3

| Compositions of the A*, G*, C* and T* Phosphoramidite Solutions | |
|---|---|
| A* | 95.7% A and 1.43% each G, C, and T |
| G* | 95.8% G and 1.4% each A, C, and T |
| C* | 95.8% C and 1.4% each A, G, and T |
| T* | 96.3% T and 1.23% each A, G, and C. |

The glucagon analog oligonucleotide library was designed to form, when annealed, a set of DNA segments encoding a series of glucagon analogs flanked by sequences that allow the insert to be directionally inserted into the expression vector such that the 5' end of the analog coding sequence is joined in frame to the alpha factor prepro sequence via a sequence encoding a KEX2 site. The sense strand of the glucagon analog library was synthesized as a set of two oligonucleotide pools. The first oligonucleotide pool contained 56 nucleotide oligomers that were synthesized to include, at the 5' end, a 15 nucleotide unmutagenized sequence encoding a Hind III adhesive end and a bridging sequence between the Hind III site and the KEX2 cleavage site of the alpha factor prepro sequence, followed by 41 nucleotides synthesized with a mixture of correct and incorrect phosphoramidites in the ratios described above relative to the native glucagon sequence from nucleotide 1 to nucleotide 41 of FIG. 2 (Sequence ID No. 1).

The second oligonucleotide pool contained 54 nucleotide oligomers that were synthesized to include one unmutagenized base at the 3' end followed by 45 nucleotides synthesized with a mixture of correct and incorrect phosphoramidites using the ratios described above relative to the native glucagon sequence from nucleotide 43 to 87 of FIG. 3 (Sequence ID No. 1), followed by an eight nucleotide unmutagenized sequence at the 5' end encoding a stop codon followed by a sequence encoding Eco RI and Bgl II restriction sites. Given the numbers of A, G, C, and T residues and the contamination levels calculated above, the aggregate base substitution rate was calculated to be 4.1% with an average of 3.52 base substitutions per coding sequence.

Following deprotection and purification of the oligonucleotides by conventional methods, the second oligonucleotide pool was treated with ATP and T4 polynucleotide kinase to add a phosphate group to the 5' ends of the oligomers. Equimolar amounts of both oligonucleotide pools were then mixed, annealed to the antisense oligonucleotide ZC3021 (Table 1; Sequence ID Number 9), and the resulting adapters were isolated. Plasmid pBS114 was linearized by digestion with Hind III and Bgl II and was gel purified. The isolated oligonucleotide adapters were ligated to the linearized pBS114, and the ligation mixture was transformed into electroporation-competent E. coli strain DH10B ™ cells (GIBCO BRL, Gaithersburg, Md.) using a BioRad electroporation unit (BioRad Laboratories, Richmond, Calif.). Transformants were selected on LB plates containing ampicillin.

Plasmid DNA prepared from fifty transformants was analyzed by restriction enzyme digestion to determine the proportion of clones with inserts and to estimate mutation frequency. All fifty plasmids contained inserts. The mutation frequency was estimated by digesting with either Asp 718 or a mixture of Pst I and Xho I. Because the unmutagenized sequence included both an Asp 718 and an Xho I site, a subset of the mutations found in the pool could be detected as a shift in the digestion pattern of the plasmid DNA. Seven of the fifty clones lacked the Xho I site present in the wild-type sequence and three lacked the Asp 718 site. Given the contamination level of each base, the distribution of bases in Asp 718 and Xho I sites and the fact that base substitutions in the pool should be corrected by excision repair when cloned into E. coli (each base substitution was paired with the wild type base), 6 clones lacking Asp 718 sites and six lacking Xho I sites were expected in the fifty clones tested. The observed numbers are not significantly different from these predictions, but may indicate a slightly lower overall frequency of mutagenesis than expected.

The mutation frequency was also measured by determining the DNA sequence of the glucagon coding region of twelve clones selected at random. Thus a total of 1032 (86×12) mutagenized bases were examined for mutation. Twenty-eight base changes were found, for an overall rate of 2.7%. This is somewhat higher than expected (2.1%) given the base substitution rate and 50:50 chance of excision repair, but probably not statistically significant. The distribution of the mutations among the twelve sequences was such that two of the sequences were wild type, three had a single base change, four had three mutations, two had four mutations and one had five. Using the Poisson distribution and the observed average of 2.3 mutations per coding sequence one would expect coding sequences with 0, 1, 2, 3, 4, and 5 mutations to occur with the frequencies of 9.7%, 22.5%, 26.7%, 24.2%, 13.3% and 6.3% respectively. The observed numbers are reasonably consistent with these predictions except that clones with 0 or >2 mutations may be overrepresented. This may reflect the fact that the excision repair process uses one strand as template for a segment of DNA rather than correcting individual mismatched bases.

The remainder of the DH10B ™ transformants (approx. 10,000 total colonies) were pooled by washing them off the transformation plates. A portion of the resulting cell suspension was used to inoculate 250 ml of LB+ampicillin which was incubated at 37° C. overnight in an airbath shaker. Plasmid DNA was prepared from the overnight culture, and the DNA was used to transform S. cerevisiae ZY100 as described above. Colonies were selected in -URADS (Table 2). Individual URA+ colonies were streaked onto -LEUD plates (Table 2). One isolated colony was selected from each streak and patched onto a second -LEUD plate in sets of 96 per plate for storage. A total of 22 plates of approximately 96 colonies each were collected.

Two hundred to three hundred microliters of -LEU TRP THR liquid medium (Table 2) was sterilely transferred to each well of 96-well microtiter plates. Each well was inoculated with yeast from one of the patches from the -LEUD plates, and the microtiter plates were incubated at 30° C. for 40–48 hours to allow for growth of the yeast. After incubation, the plates were centrifuged for 5 minutes to clarify the yeast broths. The clarified broths were assayed as described in Example 5.

Approximately 5% of the strains that resulted in the lowest cAMP production were chosen for retest. This retest consisted of assaying the effects of culture broths on adenylate cyclase activity in duplicate with and without exogenous glucagon as described in Example 5. Broths from strains making active glucagon, such as ZB210, resulted in the stimulation of adenylate cyclase activity even in the absence of exogenous glucagon, but broths from strains making antagonists or inactive glucagon analogs should provide no stimulation above background. Upon retesting, only one strain, designated P60, consistently resulted in less cAMP production than the ZB213 control. FIG. 3 shows the cAMP response of rat liver membranes to three concentrations of glucagon in the presence of culture broth from P60 and from the control strains making des-His$^1$-glucagon and des-His$^1$-[Glu$^9$]glucagon. FIG. 3 shows that P60 is, within experimental error, as good an antagonist as des-His$^1$-glucagon. Recovery of the plasmid from this yeast strain and subsequent DNA sequence analysis showed that the analog expressed by this strain is [Ser$^4$]-glucagon. The plasmid DNA prepared from the yeast transformant was also used to transform S. cerevisiae strain ZY100 to establish a transformant containing a plasmid encoding an analog of known sequence. The ZY100 transformant containing a plasmid encoding [Ser$^4$]glucagon (P60) was given the isolation number ZB312.

A second round of screening was performed on the library of yeast strains producing glucagon analogs. Ten additional plates, each containing 96 colonies, were collected and screened as described above. Values from different experiments were normalized according to the responses observed with control strains (ZB210 and ZB213). All 960 clones were ranked according to antagonist activity, and those with cAMP values lower than ZB213 were chosen for rescreening. Rescreening was performed by growing fresh cultures and assaying the culture broths in duplicate adenylate cyclase assays in the presence of 5 nM glucagon. The results of the duplicate assays were averaged and again compared to the value obtained with ZB213. This time, only 14 strains had improved activity relative to the control. These 14 strains were then assayed in an experiment similar to that described above for P60 wherein culture broths from the strains were assayed in the presence of 0, 4, and 8 nM glucagon. Four strains yielded values that were not significantly different from those obtained with ZB213 and were removed from further consideration. Plasmids were recovered from the remaining strains and were subjected to DNA sequence analysis. Plasmid DNA prepared for sequence analysis was then transformed into strain ZY100. These transformants were given identification numbers to signify that they contained plasmid DNA encoding glucagon antagonists of known sequence. The sequence analysis showed that two strains contained identical mutant glucagons, leaving an additional nine independent clones: ZB315, ZB316, ZB317, ZB318, ZB319, ZB320, ZB321, ZB322 and ZB323 corresponding to BB25, BB64, BB65, FF21, FF30, FF93, HH33, CC29 and HH63, respectively (Table 4).

TABLE 4

| Glucagon Antagonists | | |
|---|---|---|
| Screen Number | Isolation Number | Glucagon Antagonist |
| D28 | ZB300 | des-His$^1$-[Glu$^9$-Phe$^{13}$]glucagon |
| E5 | ZB301 | des-His$^1$-[Ala$^4$]glucagon |

TABLE 4-continued

Glucagon Antagonists

| Screen Number | Isolation Number | Glucagon Antagonist |
|---|---|---|
| F59 | ZB302 | des-His$^1$-[Thr$^2$]glucagon |
| G56 | ZB303 | des-His$^1$-[Ser$^4$]glucagon |
| G60 | ZB304 | des-His$^1$-[Asn$^9$-Phe$^{13}$]glucagon |
| G68 | ZB305 | des-His$^1$-[Pro$^3$-Ser$^{29}$]glucagon |
| H21 | ZB306 | des-His$^1$-[Ala$^9$]glucagon |
| H33* | ZB307 | des-His$^1$-[Glu$^{21}$]glucagon |
| I1 | ZB308 | des-His$^1$-[Ile$^7$]glucagon |
| J15 | ZB309 | des-His$^1$-[Ala$^{11}$]glucagon |
| J36 | ZB310 | des-His$^1$-[Asn$^9$]glucagon |
| J95 | ZB311 | des-His$^1$-[Ala$^2$]glucagon |
| P60 | ZB312 | [Ser$^4$]glucagon |
| D16 | ZB313 | des-His$^1$-[Glu$^{21}$-Ser$^{29}$]glucagon |
| F73** | ZB314 | des-His$^1$-[Ser$^{29}$]glucagon |
| BB25 | ZB315 | [Cys$^2$]glucagon |
| BB64 | ZB316 | [His$^3$-Ser$^4$]glucagon |
| BB65 | ZB317 | [Asp$^1$-Ala$^2$-Ile$^7$]glucagon |
| FF21 | ZB318 | [Pro$^2$]glucagon |
| FF30 | ZB319 | [Asp$^4$-Ser$^5$]glucagon |
| FF93 | ZB320 | [Asn$^{10}$-Tyr$^{21}$]glucagon |
| HH33 | ZB321 | des-Arg$^{18,19}$-[Leu$^{16}$-Leu$^6$-Asn$^{13}$-Thr$^{16}$]glucagon |
| CC29 | ZB322 | des-26-29-[Leu$^{16}$-Gly$^{2l}$-Ser$^{22}$-Arg$^{25}$]glucagon |
| HH63*** | ZB323 | [Gly$^{23}$]glucagon |
| K41 | ZB324 | des-His$^1$-[Glu$^9$-His$^{24}$]glucagon |
| K93 | ZB325 | des-His$^1$-[Ser$^5$]glucagon |
| O84 | ZB326 | des-His$^1$-[Asn$^9$-Leu$^{27}$]glucagon |
| M28 | ZB327 | des-His$^1$-[Ser$^4$-Ala$^{29}$]glucagon |
| M14 | ZB328 | des-His$^1$-[Glu$^9$-Ala$^{11}$]glucagon |

*The glucagon antagonist produced by ZB307 is identical to the antagonist produced by B6.
**The glucagon antagonist produced by ZB314 is identical to the antagonist produced by D45.
***The glucagon antagonist produced by ZB323 includes the C-terminal extension Glu-Phe-Arg-Ser-Arg-Tyr-Leu-Glu-Thr-Lys-Ile-Asn-Ile-Ile-Ile

Example 4

Construction of a Des-His$^1$-glucagon Analog Oligonucleotide Library

A des-His$^1$-glucagon analog oligonucleotide library was constructed similarly to the glucagon analog oligonucleotide library described in Example 3 except that both strands were mutagenized. A set of four synthetic oligonucleotide pools were designed to provide a series of DNA sequences encoding des-His$^1$-glucagon analogs flanked by sequences that allow directional insertion into the expression vector such that the 5' end of the analog coding sequence is joined in frame to the alpha factor prepro sequence via a KEX2 cleavage site sequence.

The antisense strand of the des-His$^1$-glucagon analog library was prepared as a set of two pools of oligonucleotides. The first oligonucleotide pool contained 61 nucleotide oligomers that were synthesized to include, from the 3' end, an eleven nucleotide unmutagenized sequence complementary to a sequence bridging the Hind III site of the alpha factor prepro sequence and a KEX2 cleavage site sequence, followed by 50 nucleotides synthesized with a mixture of correct and incorrect phosphoramidites in a 97:1:1:1 ratio relative to the antisense strand of the native glucagon sequence, from nucleotide 4 to nucleotide 53 of FIG. 2 (Sequence ID Nos. 1 and 2).

The second oligonucleotide pool contained 46 nucleotide oligomers that were synthesized to include one unmutagenized base at the 3' end followed by 33 nucleotides synthesized with a mixture of correct and incorrect phosphoramidites in a 97:1:1:1 ratio relative to the antisense strand of the native glucagon sequence from nucleotide 55 to nucleotide 87 of FIG. 3 (Sequence ID No. 1), followed by a 12 nucleotide unmutagenized sequence at the 5' end, which contained a sequence complementary to a stop codon followed by a sequence containing Eco RI and Bgl II restriction sites.

The sense strand of the des-His$^1$-glucagon analog library was also prepared as a set of two pools of oligonucleotide sequences. The first oligonucleotide pool contained 54 nucleotide oligomers which were synthesized to include a 20 nucleotide unmutagenized sequence including a 5' Hind III adhesive end followed by the sequence between the Hind III site and the KEX2 cleavage site sequence of the alpha factor prepro sequence, followed by 38 nucleotides synthesized with a mixture of correct and incorrect phosphoramidites in a 97:1:1:1 ratio relative to the native glucagon sequence from nucleotide 4 to nucleotide 41 of FIG. 3 (Sequence ID No. 1).

The second oligonucleotide pool contained 46 nucleotide oligomers which were synthesized to include one unmutagenized base at the 3' end followed by 45 nucleotides synthesized with a mixture of correct and incorrect phosphoramidites in a 97:1:1:1 ratio relative to the native glucagon sequence from nucleotide 43 to nucleotide 87 of FIG. 3 (Sequence ID No. 1), followed by an 8 nucleotide unmutagenized sequence at the 5' end, which included a stop codon followed by Eco RI and Bgl II restriction sites.

The four oligonucleotide pools were annealed, ligated and transformed as described in Example 3. The resulting des-His$^1$-glucagon analog oligonucleotide library was transformed into *Saccharomyces cerevisiae* strain ZY100 and the *Sacchromyces cerevisiae* library was prepared as described above.

One isolate from the des-His$^1$-glucagon pool was sequenced and confirmed to encode des-His$^1$-glucagon. This plasmid was transformed into *Saccharomyces cerevisiae* strain ZY100 to create the strain ZB117. Strain ZB117 was used as the control strain for producing unmodified des-His$^1$-glucagon.

Approximately 900 individual yeast clones transformed with pooled plasmid DNA from the des-His$^1$-glucagon oligonucleotide library were screened as described in Example 3. Broth from approximately 35% of these yeast clones resulted in reduced cAMP production as compared to the ZB213 (no glucagon) control. However, since des-His$^1$-glucagon is itself a weak antagonist, more stringent screening criteria were used. Clones which produced des-His$^1$-glucagon analogs that reduced the production of cAMP more than one standard deviation below the average amount (approximately 20% of the total) were selected for rescreening. The rescreened broths were assayed in duplicate, and the results were averaged. Approximately one quarter of these rescreened clones, which consistently produced des-His$^1$-glucagon analogs that produced less adenyl cyclase activity stimulation than the des-His$^1$-glucagon producing control strain ZB217, were selected for further analysis. Plasmid DNA was prepared from yeast strains selected for further analysis as described above. The plasmid DNA was subjected to DNA sequence analysis and was used to transform *S. cerevisiae* strain ZY100. The transformants containing plasmids encoding glucagon antagonists of known sequence were given isolation numbers (Table 4).

A second round of screening was performed on the mutant des-His$^1$-glucagon analog library as described above. Five additional clones, given isolation numbers ZB324 through ZB328 (Table 4), were identified as producing glucagon analogs producing less adenyl cyclase stimulation than the des-His$^1$-glucagon producing control strain ZB217.

Further experiments included the type of response curve described in Example 5 wherein yeast broth is used to inhibit the response of hepatocyte membrane adenylate cyclase to three concentrations of glucagon. At least ten yeast clones producing glucagon analogs that are more effective antagonists than des-His$^1$-glucagon were identified in these experiments. When the amount of yeast broth used was normalized to its immunoreactivity in a glucagon radioimmuno assay, several clones appeared to make antagonists that are even more effective than the des-His$^1$-[Glu$^9$]-glucagon analog made by ZB216. These antagonists are identified in Table 5. FIG. 4 shows the cAMP response of rat liver membranes to three concentrations of glucagon in the presence of culture broth from B6 and J15 and from the control strains making des-His$^1$-glucagon and des-His$^1$-[Glu$^9$]glucagon. FIG. 4 shows that B6 and J15 are better antagonists relative to both des-His$^1$-glucagon and des-His$^1$-[Glu$^9$]glucagon.

TABLE 5 des-His$^1$-[Glu$^{21}$]glucagon
des-His$^1$-[Ala$^{11}$]glucagon
des-His$^1$-[Pro$^3$-Ser$^{29}$]glucagon
des-His$^1$-[Ile$^7$]glucagon
des-His$^1$-[Glu$^9$-Phe$^{13}$]glucagon
des-His$^1$-[Ser$^{29}$]glucagon
des-His$^1$-[Asn$^9$-Phe$^{13}$]glucagon
des-His$^1$-[Ala$^9$]glucagon
des-His$^1$-[Glu$^{21}$-Ser$^{29}$]glucagon
des-His$^1$-[Asn$^9$]glucagon
des-His$^1$-[Set$^4$]glucagon
des-His$^1$-[Thr$^2$]glucagon

Example 5

Glucagon Antagonist Screening Assay

A. Preparation of Rat Liver Membranes

Young female Sprague-Dawley rats were used for the preparation of liver membranes using the method essentially described by Neville (ibid.) and modified by Pohl et al. (ibid). Ten to 15 rats yielding 60-100 grams of liver were processed per batch. After the rats were euthanized by cervical dislocation, their livers were surgically removed and transferred, as quickly as possible, to an iced beaker. Scissors were used to mince the tissue into pieces approximately 3-6 mm in size. Any connective tissue that was present was removed.

The minced tissue was suspended in ice cold 1 mM sodium bicarbonate at a concentration of approximately 300 g/l. This suspension was processed in batches in a tissue homogenizer with eight strokes of the loose pestle. The homogenate was mixed with additional ice cold 1 mM sodium bicarbonate to yield a final concentration of about 40-80 g/l. After stirring the diluted homogenate for at least three minutes, it was filtered through a double layer of cheese cloth. The filtrate was refiltered through four layers of cheese cloth, transferred to centrifuge bottles and centrifuged at 1500×g for 30 minutes at 4° C.

After centrifugation, as much of the supernatant as possible was carefully decanted and discarded, and the pellets were gently resuspended in the remaining supernatant with three strokes of the loose pestle in a clean tissue homogenizer. The volume of the resuspended supernatant was adjusted to 72 ml with water, and 93 ml of 69% (w/w) sucrose was added to yield 165 ml of membrane suspension in 44% sucrose. After thorough mixing, the sucrose concentration was measured with a refractometer and adjusted to between 43.9% and 44.1% sucrose (corresponding to a refractive index between 1.4076 and 1.4080) with either 69% sucrose or water. The adjusted suspension was distributed into six 1"×3.5" cellulose nitrate tubes, and the tubes were filled and balanced by overlaying with a fresh sucrose solution which had been adjusted to a concentration between 42.2% and 42.4% sucrose (corresponding to a refractive index between 1.4042 and 1.4046). The samples were centrifuged in a Beckman SW28 swinging bucket ultracentrifuge rotor at 25,000 rpm for 150 minutes at 4° C.

The purified membranes were recovered as a layer floating at the top meniscus of the tubes. The membranes were scooped out with a spoon-shaped spatula or were removed by suction into a syringe through an 18-gauge needle. The membranes were resuspended in 10 ml of 1 mM bicarbonate by suction and expulsion from a 10-25 ml syringe through an 18-gauge or 20-gauge needle. Following resuspension, the membranes were washed by adding 60-80 ml of 1 mM bicarbonate and centrifuged at 15,000 rpm in a high speed centrifuge. The supernatants were discarded, and the pellets were resuspended in. 1 mM bicarbonate and pooled to yield approximately 5-10 ml of concentrated hepatocyte membranes. The membrane preparation was aliquoted and was stored frozen at −80° C. for up to six months.

The protein concentration of the membrane preparation was determined by diluting 10-20 μl of the membrane preparation 100-fold in 1M NaCl, 0.17M sodium phosphate (pH 7.0) buffer. The absorbance of this solution relative to the buffer was measured in 1 cm quartz cuvettes at 224 nm and 236.5 nm wave length in a UV spectrophotometer. Protein concentration was calculated according to the formula:

$$A_{224nm} - A_{236.5nm} = (mg/ml\ protein)(6.45)(100)$$

B. Adenylate cyclase reaction:

The adenylate cyclase assay was carried out by first adding 5 μl of sample (e.g. yeast broth) containing potential inhibitors at micromolar concentrations to each well of a 96-well microtiter plate. An A+B solution was prepared by mixing 2.5 ml of Solution A (Table 6) with 2.5 ml of Solution B (Table 6). Fifty microliters of the A+B solution was added to each "no glucagon" control well. Glucagon was added from the "G" solution to the remaining A+B solution to a concentration of 1×10$^{-8}$M (this results in a final assay concentration of 5×10$^{-9}$). Fifty microliters of the A+B+glucagon solution was added to each well, excluding the "no glucagon" controls. The membrane preparation was diluted to approximately 2 mg/ml protein with water. The reaction was started by the addition of 45 μl of diluted membrane to each well, in order. The assays were incubated for 12 minutes at room temperature, and were stopped by the addition of 100 μl of Stop Mix to each well in the same order that the diluted membrane was added. The assay mixtures were clarified by centrifugation, and the assays were stored at 4° C.

Table 6
Reagent Recipes

Solution A
100 mM Tris HCl pH 7.6
20 mM MgCl$_2$
0.4% BSA
4 mg/ml Creatine Phosphokinase (Sigma Chemical Company)
Solution B
4 mM ATP
20 mM GTP
4 mM isobutyl-1-methyl-xanthine (IBX; Sigma Chemical Co.)
4 mM EDTA
120 mM Creatine Phosphate
"G"
1 mM glucagon
Stop MiX
100 mM Acetic acid
50 mM EDTA

C. Cyclic AMP Assay

Cyclic AMP concentrations were determined using an Amersham Scintillation Proximity Assay Kit (Amersham, Arlington Heights, Ill.). Briefly, 10 μl from each adenylate cyclase reaction was added to individual beta plate wells. Each sample was diluted with 65 μl of 50 mM Na Acetate. Cyclic AMP standards were prepared at 0.0, 1.6 and 6.4×10$^{-9}$M or may be prepared from the "non-acetylation standards" supplied with Amersham kit. Triplicate standards of 75 μl of each standard were added to individual beta plate wells. Nonspecific binding (NSB) controls were prepared by adding 150 μl of 50 mM Na Acetate to triplicate beta plate wells. Seventy-five microliters of $^{125}$I-cAMP (approx. 0.45 mCi/ml) was added to each well, followed by the addition of 75 μl of diluted rabbit anti-succinyl cAMP antiserum (diluted per manufacturer's instruction in 50 mM Na Acetate) to each well, excluding the NSB controls. Seventy-five microliters of diluted anti-rabbit SPA reagent was then added to each well, and the plates were sealed and incubated, with shaking, overnight at room temperature. The plates were counted for one minute per sample in a beta-plate counter. Mean counts were computed for the NSB controls and the standards. The percent response for the standards and samples was determined using the formula:

$$\%R_X = (CPM - CPM_{NSB})/(CPM_{0.0} - CPM_{NSB})$$

where

%R$_X$=Percent response for a given sample or standard
CPM=Sample counts
CPM$_{NSB}$=Mean NSB control counts
CPM$_{0.0}$=Mean 0.0M standard counts The relative concentration of cAMP for a given sample was determined using the formula:

$$cAMP]_x = 1.6e^{ln4(\%Rx - \%R1.6)/(\%R6.4 - \%R1.6)}$$

where

[cAMP]$_x$=the relative concentration of a given sample
%Rx=Percent response for a given sample
%R1.6=Percent response for the 1.6×10$^{-9}$M standard
%R6.4=Percent response for a the 6.4×10$^{-9}$M standard Potential antagonists were identified as those which inhibited the stimulation of the rat liver membrane adenylate cyclase by glucagon. Thus, assay wells that contained significantly less cAMP than wells containing broth from a control strain that does not produce glucagon (ZB213) should correspond to yeast strains that produce glucagon analogs with antagonist activity. Because of a relatively high degree of variability in the values obtained for control and mutant strains, an average cAMP value was computed for all samples on a given plate, and those yeast strains which corresponded to values significantly less than this average were selected for further study.

Example 6
Synthetic Peptide Glucagon Antagonists

The peptides [Ser$^4$]glucagon, des-His$^1$-[Ser$^4$]glucagon, des-His$^1$-[Glu$^{21}$]glucagon, des-His$^1$-Ser$^{29}$]glucagon, des-His$^1$-[Ala$^{11}$]glucagon and [Asp$^1$-Ala$^2$-Ile$^7$]-glucagon were synthesized on an Applied Biosystems (Foster City, Calif.) Model 431A peptide synthesizer using standard cycles as directed by the manufacturer and Fmoc chemistry essentially as described by Carpino and Hah (J. Amer. Chem. Soc. 92:5748-5749, 1970; J. Org. Chem. 37:3404-3409, 1972). An unloaded HMP (p-alkyloxybenzyl alcohol) resin was used. The first amino acid was coupled to the resin as a symmetric anhydride. Subsequent amino acids were coupled as HOBt active esters. After each coupling, a capping cycle with acetic anhydride was run to minimize the occurrence of deletion peptides. When the synthesis was complete, the final Fmoc protecting group was removed and the resin dried. During synthesis, a resin sample was taken after each coupling. Samples were assayed as directed by the manufacturer. The first sample was used to test the efficiency of the resin loading. The efficiency of coupling was assayed using a ninhydrin assay. Peptides were cleaved from the resin using 95% trifluoroacetic acid (TFA), precipitated in diethyl ether and redissolved in 10% acetic acid. Peptides were purified by reverse-phase HPLC using a Vydac C-4 column (The Separations Group, Hesperia, Calif.) with a H$_2$O/acetonitrile (both containing 0.1% TFA) gradient. For each peptide, the main peak was collected, a sample was taken for amino acid analysis, and the peptide was lyophilized.

The peptides were dissolved in water at 1 mM concentration based upon a molar extinction coefficient of 8290 at a wavelength of 278 nm. Serial dilution in water then provided a range of concentrations that could be tested for effects on adenylate cyclase activity as described in Example 5. Peptides were tested alone and in the presence of 20 nm glucagon. Only [Ser$^4$]glucagon showed stimulation of adenylate cyclase activity in the absence of added glucagon, and this stimulation was slight and occurred only at the highest concentration assayed (10 μM final in the reaction mixture). All the synthetic analogs (including [Ser$^4$]glucagon) were able to effectively inhibit the response to glucagon in a dose-dependent manner. Data from these experiments were used to estimate an inhibition coefficient (I/A$_{50}$) for each of these analogs as shown in Table 7. I/A$_{50}$ is defined as the ratio of inhibitor to agonist concentration wherein the response is reduced to one-half of that observed with the agonist alone.

TABLE 7

| Analog | (I/A$_{50}$) |
|---|---|
| [Ser$^4$]glucagon | 35 |
| des-His$^1$-[Ser$^4$]glucagon | 25 |
| des-His$^1$-[Ala$^{11}$]glucagon | 18 |

TABLE 7-continued

| Analog | (I/A$_{50}$) |
|---|---|
| des-His$^1$-[Glu$^{21}$]glucagon | 22 |
| des-His$^1$-[Ser$^{29}$]glucagon | 30 |
| [Asp$^1$-Ala$^2$-Ile$^7$]glucagon | 25 |

We claim:

1. A glucagon antagonist produced from a host cell containing a DNA construct capable of directing the expression of a glucagon antagonist, the construct comprising the following operationally linked elements: a transcriptional promoter, a secretory sequence, a DNA sequence encoding a glucagon antagonist, wherein the sequence encodes one or more amino acids that are different from the corresponding amino acid residues in native glucagon, and a transcriptional promoter wherein the glucagon antagonist is selected from the group consisting of des-His$^1$-[Glu$^{21}$]glucagon, des-His$^1$-[Glu$^{21}$-Ser$^{29}$]glucagon, des-His$^1$-[Glu$^9$-Phe$^{13}$]glucagon, des-His$^1$-[Ser$^{29}$]glucagon, des-His$^1$-[Thr$^2$]glucagon, des-His$^1$-[Ala$^{11}$]glucagon, des-His$^1$-[Asn$^9$-Phe$^{13}$]glucagon, des-His$^1$-[Pro$^3$-Ser$^{29}$]glucagon, [Ser$^4$]-glucagon, des-His$^1$-[Ala$^9$]glucagon, [Cys$^2$]glucagon, des-$^{26\text{-}29}$-[Leu$^{16}$-Gly$^{21}$-Ser$^{22}$-Arg$^{25}$]glucagon, [Gly23]glucagon, des-His$^1$-[Glu$^9$-His$^{24}$]glucagon, des-His$^1$-[Ser$^5$]glucagon, des-His$^1$-[Asn$^9$-Leu$^{27}$]glucagon, des-His$^1$-[Ser$^4$-Ala$^{29}$]glucagon, [His$^3$-Ser$^4$]glucagon, [Asp$^1$-Ala$^2$-Ile$^7$]glucagon, [Pro$^2$]glucagon, [Asp$^4$-Ser$^5$]glucagon, [Asn$^{10}$-Tyr$^{21}$]glucagon, des-Arg$^{18,19}$-[Leu$^1$-Leu$^6$-Asn$^{13}$-Thr$^{16}$]glucagon, des-His$^1$-[Ala$^4$]glucagon, des-His$^1$-[Ser$^4$]glucagon, des-His$^1$-[Asn$^9$]glucagon, des-His$^1$-[Ala$^2$]glucagon, and des-His$^1$-[Glu$^9$-Ala$^{11}$]glucagon.

2. A glucagon antagonist selected from the group consisting of des-His$^1$-[Glu$^{21}$]glugagon, des-His$^1$-[Glu$^{21}$-Ser$^{29}$]glucagon, des-His$^1$-[Glu$^9$-phe$^{13}$]glucagon, des-His$^1$-Ser$^{29}$]glucagon, des-His$^1$-[Thr$^2$]glucagon, des-His$^1$-[Ala$^{11}$]glucagon, des-His$^1$-[Asn$^9$-Phe$^{13}$]glucagon, des-His$^1$-[Pro$^3$-Ser$^{29}$]glucagon, [Ser$^4$]-glucagon, des-His$^1$-[Ala$^9$]glucagon, [Cys$^2$]glucagon, des-$^{26\text{-}29}$-[Leu$^{16}$-Gly$^{21}$-Ser$^{22}$-Arg$^{25}$]glucagon, [Gly23]glucagon, des-His$^1$-[Glu$^9$-His$^{24}$]glucagon, des-His$^1$-[Ser$^5$]glucagon, des-His$^1$-[Asn$^9$-Leu$^{27}$]glucagon, des-His$^1$-[Ser$^4$-Ala$^{29}$]glucagon des-His$^1$-[Ala$^4$]glucagon, des-His$^1$-[Ser$^4$]glucagon, des-His$^1$-[Ile$^7$]glucagon, des-His$^1$-[Asn$^9$]glucagon, des-His$^1$-[Ala$^2$]glucagon, [His$^3$-Ser$^4$]glucagon, [Asp$^1$-Ala$^2$-Ile$^7$]glucagon, [Pro$^2$]glucagon, [Asp$^4$-Ser$^5$]glucagon, [Asn$^{10}$-Tyr$^{21}$]glucagon, des-Arg$^{18,19}$-[Leu$^1$-Leu$^6$-Asn$^{13}$-Thr$^{16}$]glucagon, and des-His$^1$-[Glu$^9$-Ala$^{11}$]glucagon.

3. A glucagon antagonist selected from the group consisting of des-His$^1$-[Glu$^{21}$]glucagon, des-His$^1$-[Ala$^{11}$]glucagon, des-His$^1$-[Pro$^3$-Ser$^{29}$]glucagon, des-His$^1$-[Ile$^7$]glucagon, des-His$^1$-[Glu$^9$-Phe$^{13}$]glucagon, des-His$^1$-[Ser$^{29}$]glucagon, des-His$^1$-[Asn$^9$-Phe$^{13}$]glucagon, des-His$^1$-[Ala$^9$]glucagon, des-His$^1$-[Glu$^{21}$-Ser$^{29}$]glucagon, des-His$^1$-[Asn$^9$]glucagon, des-His$^1$-[Ser$^4$]glucagon, and des-His$^1$-[Thr$^2$]glucagon.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 87 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: N ( i v ) ANTI-SENSE: N ( i x ) FEATURE:
        ( A ) NAME/KEY: CDS
        ( B ) LOCATION: 1..87
        ( D ) OTHER INFORMATION:

( x i ) SEQUENCE DESCRIPTION: SEQ ID NO:1:

```
CAC TCT CAA GGT ACC TTT ACC TCT GAC TAC TCT AAG TAT CTA GAC TCG      48
His Ser Gln Gly Thr Phe Thr Ser Asp Tyr Ser Lys Tyr Leu Asp Ser
  1               5                  10                  15

AGG CGT GCT CAA GAC TTT GTT CAA TGG TTG ATG AAT ACC                  87
Arg Arg Ala Gln Asp Phe Val Gln Trp Leu Met Asn Thr
         20                  25
```

( 2 ) INFORMATION FOR SEQ ID NO:2:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
His Ser Gln Gly Thr Phe Thr Ser Asp Tyr Ser Lys Tyr Leu Asp Ser
  1               5                  10                  15

Arg Arg Ala Gln Asp Phe Val Gln Trp Leu Met Asn Thr
         20                  25
```

( 2 ) INFORMATION FOR SEQ ID NO:3:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: N ( i v ) ANTI-SENSE: N ( v i i ) IMMEDIATE SOURCE:
        ( B ) CLONE: ZC1159

( x i ) SEQUENCE DESCRIPTION: SEQ ID NO:3:

TTGTCCAAGC TTACACCTTC                                                              20

( 2 ) INFORMATION FOR SEQ ID NO:4:

( i ) SEQUENCE CHARACTERISTICS:
           ( A ) LENGTH: 82 bases
           ( B ) TYPE: nucleic acid
           ( C ) STRANDEDNESS: single
           ( D ) TOPOLOGY: linear ( i i ) MOLECULE TYPE: other nucleic acid ( i i i ) HYPOTHETICAL: N ( i v ) ANTI-SENSE: N ( v i i ) IMMEDIATE SOURCE:
           ( B ) CLONE: ZC1197

( x i ) SEQUENCE DESCRIPTION: SEQ ID NO:4:

AGCTTGGACA AGAGAGTTGT TTCTCACTTC AACGACTGTC CAGACCCTCA CACCCAATTC    60

TGTTTCCACG GTACCTGTAC AT                                            82

( 2 ) INFORMATION FOR SEQ ID NO:5:

( i ) SEQUENCE CHARACTERISTICS:
           ( A ) LENGTH: 85 bases
           ( B ) TYPE: nucleic acid
           ( C ) STRANDEDNESS: single
           ( D ) TOPOLOGY: linear ( i i ) MOLECULE TYPE: other nucleic acid ( i i i ) HYPOTHETICAL: N ( i v ) ANTI-SENSE: N ( v i i ) IMMEDIATE SOURCE:
           ( B ) CLONE: ZC1198

( x i ) SEQUENCE DESCRIPTION: SEQ ID NO:5:

TCTTGGTTCA AGAAGACAAG CCAGCATGCG TTTGTCACTC TGGTTACGTT GGTGCTAGAT    60

GTGAACACGC TGTGTTGGCT TAAAT                                         85

( 2 ) INFORMATION FOR SEQ ID NO:6:

( i ) SEQUENCE CHARACTERISTICS:
           ( A ) LENGTH: 84 bases
           ( B ) TYPE: nucleic acid
           ( C ) STRANDEDNESS: single
           ( D ) TOPOLOGY: linear ( i i ) MOLECULE TYPE: other nucleic acid ( i i i ) HYPOTHETICAL: N ( i v ) ANTI-SENSE: N ( v i i ) IMMEDIATE SOURCE:
           ( B ) CLONE: ZC1199

( x i ) SEQUENCE DESCRIPTION: SEQ ID NO:6:

CCAACAATGT ACAGGTACCG TGGAAACAGA ATTGGGTGTG AGAGTCTGGA CAGTCGTTGA    60

AGTGAGAAAC AACTCTCTTG TCCA                                          84

( 2 ) INFORMATION FOR SEQ ID NO:7:

( i ) SEQUENCE CHARACTERISTICS:
           ( A ) LENGTH: 86 bases
           ( B ) TYPE: nucleic acid
           ( C ) STRANDEDNESS: single ( D ) TOPOLOGY: linear ( i i ) MOLECULE TYPE: other nucleic acid ( i i i ) HYPOTHETICAL: N ( i v ) ANTI-SENSE: N ( v i i ) IMMEDIATE SOURCE:
  ( B ) CLONE: ZC1200

( x i ) SEQUENCE DESCRIPTION: SEQ ID NO:7:

```
CTAGATTTAA GCCAACAAGT CAGCGTGTTC ACATCTAGCA CCAACGTAAC CAGAGTGACA      60

AACGCATGCT GGCTTGTCTT CTTGAA                                          86
```

( 2 ) INFORMATION FOR SEQ ID NO:8:

( i ) SEQUENCE CHARACTERISTICS:
    ( A ) LENGTH: 110 bases
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: N ( i v ) ANTI-SENSE: N ( v i i ) IMMEDIATE SOURCE:
    ( A ) LIBRARY: ZC3020

( x i ) SEQUENCE DESCRIPTION: SEQ ID NO:8:

```
AGCTTAGATA AGAGACACTC TCAAGGTACC TTTACCTCTG ACTACTCTAA GTATCTAGAC      60

TCGAGGCGTG CTCAAGACTT TGTTCAATGG TTGATGAATA CCTGAATTCA                110
```

( 2 ) INFORMATION FOR SEQ ID NO:9:

( i ) SEQUENCE CHARACTERISTICS:
    ( A ) LENGTH: 110 bases
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: N ( i v ) ANTI-SENSE: N ( v i i ) IMMEDIATE SOURCE:
    ( B ) CLONE: ZC3021

( x i ) SEQUENCE DESCRIPTION: SEQ ID NO:9:

```
GATCTGAATT CAGGTATTCA TCAACCATTG AACAAAGTCT TGAGCACGCC TCGAGTCTAG      60

ATACTTAGAG TAGTCAGAGG TAAAGGTACC TTGAGAGTGT CTCTTATCTA                110
```

( 2 ) INFORMATION FOR SEQ ID NO:10:

( i ) SEQUENCE CHARACTERISTICS:
    ( A ) LENGTH: 107 bases
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: N ( i v ) ANTI-SENSE: N ( v i i ) IMMEDIATE SOURCE:
    ( B ) CLONE: ZC3378

( x i ) SEQUENCE DESCRIPTION: SEQ ID NO:10:

```
AGCTTAGATA AGAGATCTCA AGGTACCTTT ACCTCTGACT ACTCTAAGTA TCTAGACTCG    60
AGGCGTGCTC AAGACTTTGT TCAATGGTTG ATGAATACCT GAATTCA                 107
```

( 2 ) INFORMATION FOR SEQ ID NO:11:

( i ) SEQUENCE CHARACTERISTICS:
        ( A ) LENGTH: 107 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: N ( i v ) ANTI-SENSE: N ( v i i ) IMMEDIATE SOURCE:
        ( B ) CLONE: ZC3443

( x i ) SEQUENCE DESCRIPTION: SEQ ID NO:11:

```
GATCTGAATT CAGGTATTCA TCAACCATTG AACAAAGTCT TGAGCACGCC TCGAGTCTAG    60
ATACTTAGAG TATTCAGAGG TAAAGGTACC TTGAGATCTC TTATCTA                 107
```